Figure 1:
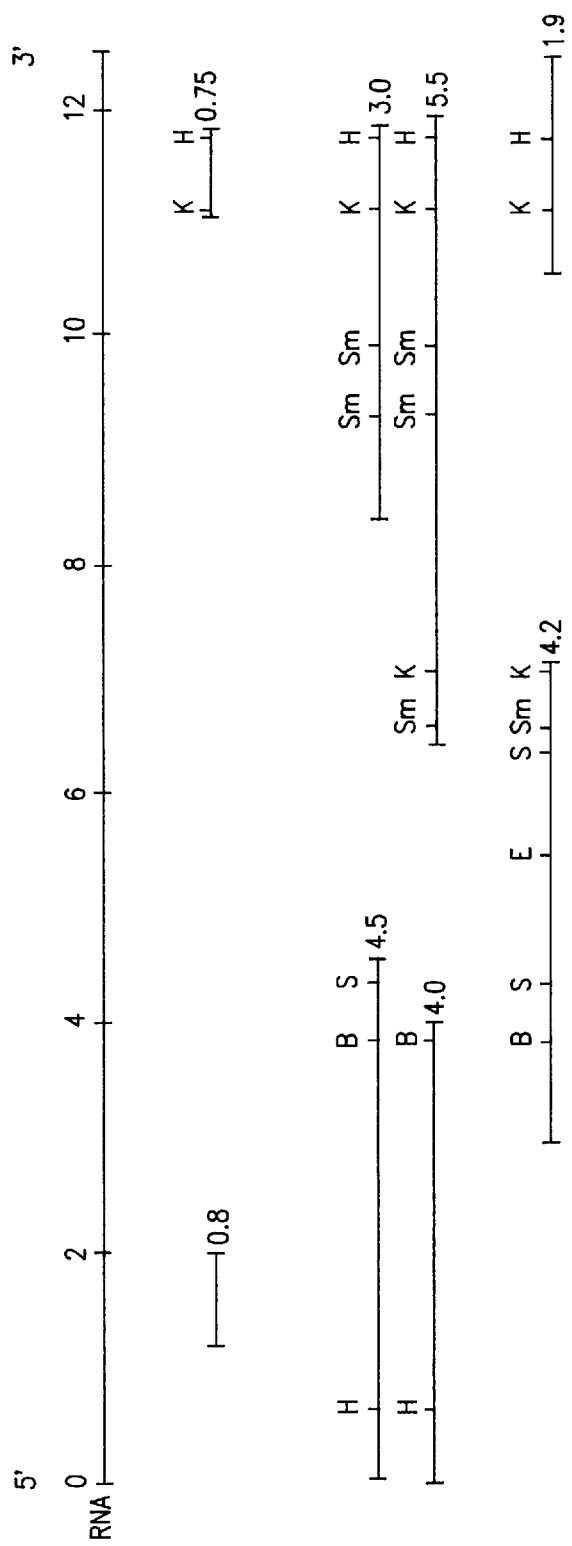

United States Patent [19]

Meyers et al.

[11] Patent Number: 5,811,103
[45] Date of Patent: Sep. 22, 1998

[54] HOG CHOLERA VIRUS VACCINE AND DIAGNOSTIC

[75] Inventors: Gregor Meyers, Stuttgart, Germany; Tillmann Rümenapf, Pasadena, Calif.; Heinz-Jurgen Thiel, Tübingen, Germany

[73] Assignee: Akzo Nobel N.V., Arnhem, Netherlands

[21] Appl. No.: 873,759

[22] Filed: Jun. 12, 1997

Related U.S. Application Data

[60] Continuation of Ser. No. 462,495, Jun. 5, 1995, abandoned, which is a division of Ser. No. 123,596, Sep. 20, 1993, abandoned, which is a continuation of Ser. No. 797,554, Nov. 22, 1991, abandoned, which is a continuation-in-part of Ser. No. 494,991, Mar. 16, 1990, abandoned.

[30] Foreign Application Priority Data

Mar. 19, 1989 [EP] European Pat. Off. ............... 89104921

[51] Int. Cl.⁶ ..................... A61K 39/187; A61K 39/00; A61K 39/38
[52] U.S. Cl. .................... 424/220.1; 424/184; 424/192.1
[58] Field of Search .......................... 424/220.1, 184.1, 424/192.1

[56] References Cited

FOREIGN PATENT DOCUMENTS 0236 977   9/1987   European Pat. Off. .
WO91/00352  1/1991   WIPO .

OTHER PUBLICATIONS

A.L. Fernelius et al., *Can. J. Comp. Med.*, 37:96–102, Jan. 1973.
R. Rümenapf et al., *Virology*, 171:18–27 (1989).
G. Meyers et al., *Virology*, 171:555–567 (1989).
M.C. Collett et al., *J. Gen. Virol.* 70:253–266 (1989).
R.J.M. Moormann et al., *Virus Research*, 11:281–291 (1988).
H.M. Geysen et al., *Journal of Immunological Methods*, 102 (1987) 259–274.

*Primary Examiner*—Lynette F. Smith
*Attorney, Agent, or Firm*—Mary E. Gormley

[57] ABSTRACT

The present invention is concerned with a hog cholera virus vaccine comprising a polypeptide characteristic of hog cholera virus. Vector vaccines capable to express a nucleic acid sequence encoding such a polypeptide also form part of the present invention. Said polypeptide and nucleic acid sequence can also be used for the detection of hog cholera virus infection.

10 Claims, 2 Drawing Sheets

FIG. I

HOG CHOLERA VIRUS VACCINE AND DIAGNOSTIC

This is a continuation of U.S. Ser. No. 08/462,495, filed Jun. 5, 1995, now abandoned, which is a divisional of U.S. Ser. No. 08/123,596, filed Sep. 20, 1993, now abandoned, which is a file wrapper continuation of U.S. Ser. No. 07/797,554, filed Nov. 22, 1991, now abandoned, which is a continuation-in-part of U.S. Ser. No. 07/494,991, filed Mar. 16, 1990, now abandoned.

The present invention is concerned with a nucleic acid sequence, a recombinant nucleic acid molecule comprising such a nucleic acid sequence, a recombinant expression system comprising such a recombinant nucleic acid molecule, a polypeptide characteristic of the hog cholera virus, a vaccine comprising such a polypeptide or recombinant expression system as well as a method for the preparation of such vaccines.

Classical swine fever or hog cholera (HC) represents an economically important disease of swine in many countries worldwide. Under natural conditions, the pig is the only animal known to be susceptible to HC. Hog cholera is a highly contagious disease which causes degeneration in the walls of capillaries, resulting in hemorrhages and necrosis of the internal organs. In the first instance hog cholera is characterized by fever, anorexia, vomiting and diarrhea which can be followed by a chronic course of the disease characterized by infertility, abortion and weak offsprings of sows. However, nearly all pigs die within 2 weeks after the first symptoms appear.

The causative agent, the hog cholera virus (HCV) has been shown to be structurally and serologically related to bovine viral diarrhea virus (BVDV) of cattle and to border disease virus (BDV) of sheep. These viruses are grouped together into the genus pestivirus within the family togaviridae. The nature of the genetic material of pestiviruses has long been known to be RNA, i.e. positive-strand RNA which lacks significant polyadenylation. The HCV probably comprises 3–5 structural proteins of which two are possibly glycosylated. The number of non-structural viral proteins is unknown.

Modified HCV vaccines (comprising attenuated or killed viruses) for combating HC infection have been developed and are presently used. However, infection of tissue culture cells to obtain HCV material to be used in said modified virus vaccines, leads to low virus yields and the virions are hard to purify. Modified live virus vaccines always involve the risk of inoculating animals with partially attenuated pathogenic HCV which is still pathogenic and can cause disease in the inoculated animal or offspring and of contamination by other viruses in the vaccine. In addition the attenuated virus may revert to a virulent state.

There are also several disadvantages using inactivated vaccines, e.g. the risk of only partial inactivation of viruses, the problem that only a low level of immunity is achieved requiring additional immunizations and the problem that antigenic determinants are altered by the inactivation treatment leaving the inactivated virus less immunogenic.

Furthermore, the usage of modified HCV vaccines is not suited for eradication programmes.

Until now, according to our knowledge diagnostic tests in swine which can distinguish between HCV or BVDV infection are not available. This is important as BVDV infection in pigs is of lower significance than HCV infection which means that BVDV infected pigs do not have to be eradicated.

Vaccines containing only the necessary and relevant HCV immunogenic material which is capable of eliciting an immune response against the pathogen do not display above-mentioned disadvantages of modified vaccines.

According to the present invention a nucleic acid sequence encoding a polypeptide characteristic of hog cholera virus has been found. Fragments of said nucleic acid sequence or said polypeptide are also within the present invention. Both the nucleic acid sequence and the polypeptide or fragments thereof can be used for the preparation of a vaccine containing only the necessary and relevant immunogenic material for immunizing animals against HCV infection. "Nucleic acid sequence" refers both to a ribonucleic acid sequence and a deoxy-ribonucleic acid sequence.

A nucleic acid sequence according to the present invention is shown in [SEQ ID NO: 1]. As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in [SEQ ID NOS: 1 and 2] use can be made of a nucleic acid sequence with such an alternative codon composition different from the nucleic acid sequence shown in [SEQ ID NO: 1].

Also included within the scope of the invention are nucleic acid sequences which hybridize under stringent conditions to the nucleic acid sequence shown in [SEQ ID NO: 1]. These nucleic acid sequences are related to the nucleic acid sequence shown in [SEQ ID NO: 1] but may comprise nucleotide substitutions, mutations, insertions, deletions etc. and encode polypeptides which are functionally equivalent to the polypeptide shown in [SEQ ID NOS: 1 and 2], i.e. the amino acid sequence of a related polypeptide is not identical with the amino acid sequence shown in [SEQ ID NOS: 1 and 2] but features corresponding immunological properties characteristic for HCV.

Within the scope of the invention are also polypeptides encoded by such related nucleic acid sequences.

The nucleic acid sequence shown in [SEQ ID NO: 1] is a cDNA sequence derived from the genomic RNA of HCV. This continuous sequence is 12284 nucleotides in length, and contains one long open reading frame (ORF), starting with the ATG codon at position 364 to 366 and ending with a TGA codon as a translational stop codon at position 12058 to 12060. This ORF consists of 3898 codons capable of encoding 435 kDa of protein.

In vivo, during HCV replication in an infected cell, this protein is synthesized as a polyprotein precursor molecule which is subsequently processed to fragment polypeptides by (enzymatic) cleavage of the precursor molecule. These fragments form after possible post-translational modifications the structural and non-structural proteins of the virus. A preferred nucleic acid sequence contains the genetic information for such a fragment with immunizing properties against HCV or immunological properties characteristic for HCV or contains the genetic information for a portion of such a fragment which still has the immunizing properties or the immunological properties characteristic for HCV.

The term "fragment or portion" as used herein means a DNA or amino acid sequence comprising a subsequence of one of the nucleic acid sequences or polypeptides of the invention. This fragment or portion encodes a polypeptide having one or more immunoreactive and/or antigenic determinants of a HCV polypeptide, i.e. has one or more epitopes which are capable of eliciting an immune response in pigs and/or is capable of specifically binding to a complementary antibody. Such epitope containing sequences are at least 5–8 residues long (Geysen, H. M. et al., 1987). Methods for determining usable polypeptide fragments are outlined below. Fragments or portions can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Fragment polypeptides of the polypeptide according to [SEQ ID NOS: 1 and 2] and the portions thereof, which can be used for the immunisation of animals against HC or for diagnosis of HC also form part of the present invention. A fragment-coding region is located within the amino acid position about 1–249, 263–487, 488–688 or 689–1067. The 1–249 region essentially represents the core protein whereas the 263–487, 488–688 and 689–1067 regions essentially represent glycoproteins of 44/48 kD, 33 kD and 55 kD respectively. Within the scope of the invention are also nucleic acid sequences comprising the genetic information for one or more of the coding regions mentioned above or portions thereof.

A preferred region to be incorporated into a vaccine against HCV infection is the region corresponding to the 55 kD protein of HCV or a portion thereof still having immunizing activity.

Furthermore, a nucleic acid sequence at least comprising the coding sequences for said 55 kD protein or portion thereof can advantageously be applied according to the present invention.

In addition, a preferred portion of the HCV 55 kD protein, which can be used for immunization of pigs against HCV infection, is determined by analyses of HCV deletion mutants with anti-55 kD protein monoclonal antibodies having virus neutralizing activity. Such a portion comprising an epitope spans the amino acid sequence about 812–859 and is coded by the nucleotide sequence about 2799–2938. A polypeptide at least comprising said amino acid sequence or a nucleic acid sequence at least comprising said nucleotide sequence form part of the present invention too.

A nucleic acid sequence according to the invention which can be used for the diagnosis of HCV infection in pigs and which can be applied to discriminate HCV from BVDV can be derived from the gene encoding the 55 kD protein.

Preferably, such a nucleic acid sequence is derived from the nucleotide sequences 2587–2619 or 2842–2880, both sequences being part of the gene encoding the 55 kD protein. A preferred oligonucleotide for diagnostic purposes is (SEQ ID NO: 3 and 4, respectively):

variations between different strains or other derivatives, are possible while retaining the same immunologic properties. These variations may be demonstrated by (an) amino acid difference(s) in the overall sequence or by deletions, substitutions, insertions, inversions or additions of (an) amino acid(s) in said polypeptide.

Moreover, the potential exists, in the use of recombinant DNA technology, for the preparation of various derivatives of the polypeptide shown in [SEQ ID NOS: 1 and 2] or fragments thereof, variously modified by resultant single or multiple amino acid substitutions, deletions, additions or replacements, for example by means of site directed mutagenesis of the underlying DNA. All such modifications resulting in derivatives of the polypeptide shown in [SEQ ID NOS: 1 and 2] or fragments thereof are included within the scope of the present invention so long as the essential characteristic activity of said polypeptide or fragment thereof, remains unaffected in essence.

RNA isolated from pelleted virions was isolated and used for the synthesis of cDNA. This cDNA was cloned in phage λgt11 and the respective library was amplified and screened with goat anti-HCV antiserum. Two positive clones could be identified and shown to have inserts with sizes of 0,8 kb and 1,8 kb. The 0,8 kb λgt11 insert was partially sequenced (see [SEQ ID NOS: 12 and 13] and determined to be located between about 1,2 and 2,0 kb on the HCV genome (see [SEQ ID NO: 7].

A nucleic acid sequence according to the invention which can be used for the diagnosis of HCV in infected animals and which surprisingly can be applied to discriminate HCV from BVDV is represented by the nucleotide sequence 5551–5793 shown in [SEQ ID NO: 1].

Moreover, a nucleic acid sequence comprising at least a sub-sequence of said nucleotide sequence and which still can be used to differentiate between HCV and BVDV forms part of the invention.

The invention also relates to a test kit to be used in an assay, this test kit containing a nucleic acid sequence according to the invention.

Preferably the test kit comprises the nucleic acid sequence represented by the nucleotide sequence 5551–5793 shown in [SEQ ID NO: 1] or a nucleic acid sequence comprising at least a sub-sequence thereof mentioned above.

RNA isolated from pelleted virions was isolated and used for the synthesis of cDNA. This cDNA was cloned in phage λgt11 and the respective library was amplified and screened with goat anti-HCV antiserum. Two positive clones could be

```
5' - CCT ACT AAC CAC GTT AAG TGC TGT GAC TTT AAA - 3'
or
5' - TTC TGT TCT CAA GGT TGT GGG GCT CAC TGC TGT GCA CTC - 3'
```

Moreover, a nucleic acid sequence comprising at least a sub-sequence of said oligonucleotides and which still can be used to differentiate between HCV and BVDV forms part of the invention.

The invention also relates to a test kit to be used in an assay, this test kit containing a nucleic acid sequence according to the invention.

Preferably the test kit comprises an oligonucleotide mentioned above or a nucleic acid sequence comprising at least a sub-sequence thereof.

Variations or modifications in the polypeptide shown in [SEQ ID NOS: 1 and 2] or fragments thereof, such as natural identified and shown to have inserts with sizes of 0,8 kb and 1,8 kb. The 0,8 kb λgt11 insert was partially sequenced (see [SEQ ID NOS: 12 and 13] and determined to be located between about 1,2 and 2,0 kb on the HCV genome (see [SEQ ID NO: 1].

A nucleic acid sequence according to the present invention can be ligated to various vector nucleic acid molecules such as plasmid DNA, bacteriophage DNA or viral DNA to form a recombinant nucleic acid molecule. The vector nucleic acid molecules preferably contain DNA sequences to initiate, control and terminate transcription and translation. A recombinant expression system comprising a host containing such a recombinant nucleic acid molecule can be used to allow for a nucleic acid sequence according to the present invention to express a polypeptide encoded by said nucleic acid sequence. The host of above-mentioned recombinant expression system can be of procaryotic origin, e.g. bacteria such as *E.coli, B.subtilis* and Pseudomonas, viruses such as vaccinia and fowl pox virus or eucaryotic origin such as yeasts or higher eucaryotic cells such as insect, plant or animal cells.

Immunization of animals against HC can, for example, be achieved by administering to the animal a polypeptide according to the invention as a so-called "sub-unit" vaccine. The subunit vaccine according to the invention comprises a polypeptide generally in a pure form, optionally in the presence of a pharmaceutically acceptable carrier.

Small fragments are preferably conjugated to carrier molecules in order to raise their immunogenicity. Suitable carriers for this purpose are macromolecules, such as natural polymers (proteins, like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers. Polypeptides to be used in such subunit vaccines can be prepared by methods known in the art, e.g. by isolation said polypeptides from hog cholera virus, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are "vector" vaccines. A nucleic acid sequence according to the invention is integrated by recombinant techniques into the genetic material of another micro-organism (e.g. virus or bacterium) thereby enabling the micro-organism to express a polypeptide according to the invention. This recombinant expression system is administered to the animal to be immunized whereafter it replicates in the inoculated animal and expresses the polypeptide resulting in the stimulation of the immune system of the animal. Suitable examples of vaccine vectors are pox viruses (such as vaccinia, cow pox, rabbit pox), avian pox viruses (such as fowl pox virus) pseudorabies virus, adeno viruses, influenza viruses, bacteriophages or bacteria (such as *Escherichia coli* and Salmonella).

The recombinant expression system having a nucleic acid sequence according to the invention inserted in its nucleic acid sequence can for example be grown in a cell culture and can if desired be harvested from the infected cells and formed to a vaccine optionally in a lyophilized form. The genetically manipulated micro-organism can also be harvested from live animals infected with the micro-organism. Abovementioned recombinant expression system can also be propagated in a cell culture expressing a polypeptide according to the invention, whereafter the polypeptide is isolated from the culture.

A vaccine comprising a polypeptide or a recombinant expression system according to the present invention can be prepared by procedures well-known in the art for such vaccines. A vaccine according to the invention can consist inter alia of whole host, host extract, partially or completely purified polypeptide or a partially or completely purified recombinant expression system as above-mentioned.

The vaccine according to the invention can be administered in a conventional active immunization scheme: single or repeated administration in a manner compatible with the dosage formulation and in such amount as will be therapeutically effective and immunogenic. The administration of the vaccine can be done, e.g. intradermally, subcutaneously, intramusculary, intra-venously or intranasally. For parenteral administration the vaccines may additionally contain a suitable carrier, e.g. water, saline or buffer solution with or without adjuvants, stabilizers, solubilizers, emulsifiers etc.

The vaccine may additionally contain immunogens related to other diseases or nucleic acid sequences encoding these immunogens like antigens of parvovirus, pseudorabies virus, swine influenza virus, TGE virus, rotavirus, *Escherichia coli,* Bordetella, Pasteurella, Erysipelas etc. to produce a multivalent vaccine.

Polypeptides according to the present invention can also be used in diagnostic methods to detect the presence of HCV antigen or antibody in an animal. Moreover, nucleic acid sequences according to the invention can be used to produce polypeptides to be used in above-mentioned diagnostic methods or as a hybridisation probe for the detection of the presence of HCV nucleic acid in a sample.

EXAMPLE 1

Immunological Identification of cDNA Clones

Infection of cells and harvesting of virus. PK15 and $38A_1D$ cells were grown in DMEM with 10% FCS and were infected in suspension by the virulent HCV strain Alfort in a volume of 20–30 ml at a cell concentration of $5\times10^7$/ml at 37° C. for 90 min with an m.o.i. of 0.01 to 0.001 (as determined by immunofluorescence assay). Thereafter, the PK15 cells were seeded in tissue culture plates (150 mm diameter), while the suspension cells $38A_1D$ were incubated in bottles with gentle stirring (Tecnomara, Switzerland). For cDNA synthese, the tissue culture supernatant was harvested 48 hours after infection, clarified at 12,000 g, and afterwards the virus pelleted in a TFA 20 rotor (Contron, Italy) at 54,000 g for 12 hours.

Preparation of goat anti-HCV serum. A fibroblastic cell strain was established from the skin biopsy of a young goat by standard cell culture techniques. The cells were initially grown in F-10 medium with 10% FCS and later in DMEM with 10% FCS. Goat fibroblasts were infected with HCV. Over the first 26 hours p.i., the cells were washed every 8 hours 3 times with PBS and afterwards incubated in DMEM with 10% preimmune goat serum (PGS). 48 hours p.i., the tissue culture supernatant was harvested and used as stock virus. Before immunization, goat cells for 30 tissue culture dishes (150 mm diameter) were kept for 3 passages in medium with 10% PGS and then infected with the stock virus. 48 hours p.i., the goat was immunized with X-ray-inactivated pelleted virus and infected cells. Both were emulsified in Freund's adjuvant (complete for basis immunization, incomplete for booster injections) and injected subcutaneously. To obtain antibodies recognizing denatured molecules, the antigen preparations were incubated in 0.2% SDS, 3 mM DTT at 95° C. for 5 min before injection.

RNA Preparation. cDNA synthesis and cloning. RNA from virions was isolated by using the guanidine thiocyanate method described by Chirgwin et al. (1979). RNA from pelleted virions (5 $\mu$g total RNA, approximately 0.5 $\mu$g HCV RNA) and 0.1 $\mu$g of random hexanucleotide primer (Pharmacia, Sweden) in 20 $\mu$l of water were heated to 65° C. for 10 min, chilled on ice, and adjusted to first strand buffer (50 mM Tris-HCl pH 8.3; 30 mM KCl; 8 mM $MgCl_2$; 1 mM DTT, dATP, dCTP, dGTP, dTTP 1 mM each and 500 units RNAguard [Pharmacia, Sweden] per ml) in a final volume of 32 μl. 35 units of AMV reverse transcriptase (Life Sciences Inc., USA) were added. After 1 hour at 43° C. the reaction mixture was added to one vial of second strand synthesis mixture (cDNA synthesis kit, Pharmacia, Sweden). Second strand synthesis, preparation of blunt ends, and Eco RI adaptor ligation and phosphorylation were done as recommended by the supplier.

The cDNA was size-fractionated by preparative agarose gel electrophoresis. The part of the gel containing DNA molecules smaller than 0.5 kb was discarded. The remaining DNA was concentrated by running the gel reversely for 15 min and extracted from the agarose after 3 cycles of freezing and thawing with phenol.

Ethanol co-precipitated cDNA and λgt11 DNA (1 μg EcoRI digested dephosphorylated arms, Promega, USA) was ligated by 3 units of T4 DNA ligase (Pharmacia, Sweden) in a total volume of 10 μl ligase buffer (30 mM Tris-HCl pH 7.4; 10 mM $MgCl_2$; 10 mM DTT; 1 mM ATP). In vitro packaging with a commercially available extract (Packagene, Promega, USA) and infection of E. coli K12 cells, strain Y 1090, with resulting phages was performed as recommended by the supplier. The library was amplified once as described (Davis et al., 1986).

Screening of λgt11 library. Screening was basically performed as described (Young and Davis, 1983) using the Protoblot system purchased from Promega, USA (Huynh et al., 1985) and a serum dilution of $10^{-3}$. For background reduction the goat anti HCV serum was treated with E. coli lysate (strain Y1090) at 0.8 mg/ml (Huynh et al., 1985). Two positive clones having inserts of 0.8 kb and 1.8 kb, respectively could be identified.

Nick translation and Northern hybridization. 50 ng of the 0.8 kb HCV nucleic acid sequence labeled with $[\alpha^{32}P]dCTP$ (3000 Ci per mMole, Amersham Buchler, FRG) by nick translation (nick translation kit, Amersham Buchler, FRG) was hybridized to Northern filters at a concentration of 5 ng per ml of hybridization mixture (5×SSC; 1×Denhardt's; 20 mM sodium phosphate pH 6.8; 0.1% SDS and 100 μg yeast tRNA [Boehringer-Mannheim, FRG] per ml) at 68° C. for 12 to 14 hours. Membranes were then washed as described (Keil et al., 1984) and exposed at −70° C. to Kodak X-Omat AR films for varying times using Agfa Curix MR 800 intensifying screens.

The 0.8 kb nucleic acid sequence hybridized not only to intact HCV RNA but also to degradation products thereof. The 0.8 kb nucleic acid sequence did not hybridize to the 1.8 kb nucleic acid sequence, indicating that these two nucleic acid sequences correspond with fragments of the HCV genome which are not located in the same region of the genomic RNA.

Nucleotide sequencing. Subcloning of HCV specific phage DNA inserts into plasmid pEMBL 18 plus was done according to standard procedures (Maniatis et al., 1982). Single-stranded DNA of recombinant pEMBL plasmids was prepared as described (Dente et al., 1985). Dideoxy sequencing reactions (Sanger et al., 1977) were carried out as recommended by the supplier (Pharmacia, Sweden).

EXAMPLE 2

Molecular Cloning and Nucleotide Sequence of the Genome of HCV

RNA preparation, cDNA synthesis and cloning. RNA preparation, cDNA synthesis, size selection and ligation of co-precipitated cDNA and λgt10 DNA (1 μg EcoRI digested dephosphorylated arms, Promega, USA) were done as described above. In vitro packaging of phage DNA using Packagene (Promega, USA) and titration of phages on E. coli strain C 600 HFL were performed as suggested by the supplier. The library was amplified once (Davis et al., 1986), and replicas transferred to nictrocellulose membranes (Amersham Buchler, FRG) (Benton and Davis, 1977) were hybridized with oligonucleotides as described above for Northern hybridization. Screening with cDNA fragments labeled with $[\alpha^{32}P]$ dCTP by nick translation (nick translation kit, Amersham Buchler, FRG) was done as described by Benton and Davis (1977). Positive clones were plaque purified and inserts subcloned into pEMBL plasmids (Maniatis et al., 1982; Dente et al., 1985; Davis et al., 1986).

A $^{32}P$ 5'-end labeled oligonucleotide of 17 bases complementary to the RNA sequence encoding the amino acid sequence Cys Gly Asp Asp Gly Phe was used for screening a λgt10 cDNA library. This oligonucleotide which hybridized to the about 12 kb genomic RNA of HCV, identified inter alia a clone with an insert of 0.75 kb, which hybridized also to HCV RNA. This 0.75 kb nucleic acid sequence which represents a fragment of the HCV genome together with the 0.8 kb λgt11 HCV nucleic acid sequence insert were used for further library screening resulting in a set of overlapping HCV nucleic acid sequences of which the relative positions and restriction site maps are shown in FIG. 1. These nucleic acid sequence fragments of the HCV genome are located between the following nucleic acid positions 4.0 kb fragment: 27–4027
4.5 kb fragment: 54–4494
0.8 kb fragment: 1140–2002
4.2 kb fragment: 3246–7252
5.5 kb fragment: 6656–11819 and within about the following nucleic acid positions 3.0 kb fragment: 8920–11920
1.9 kb fragment: 10384–12284
0.75 kb fragment: 10913–11663

Nucleotide sequencing. For complete nucleotide sequence determination exonuclease III and nuclease S1 (enzymes from Boehringer Mannheim, FRG) were used to establish deletion libraries of HCV derived cDNA inserts subcloned into pEMBL 18+ or 19+ plasmids (Hennikoff, 1987). Dideoxy sequencing (Sanger et al. 1977) of single stranded (Dente et al., 1985) or double stranded DNA templates was carried out using the T7 polymerase sequencing kit (Pharmacia, Sweden).

From the cDNA fragments a continuous sequence of 12284 nucleotides in length could be determined as shown in [SEQ ID NO: 1]. This sequence contains one long open reading frame (ORF), starting with the ATG codon at position 364 to 366 and ending with TGA as a translational stop codon at 12058 to 12060. This ORF consists of 3898 codons capable of encoding a 435 kDa protein with an amino acid sequence shown in [SEQ ID NOS: 1 and 2]. Three nucleotide exchanges were detected as a result of differences in nucleotide sequence caused by possible heterogenicity of the virus population, two of which resulted in changes in the deduced amino acid sequence [SEQ ID NOS: 1 and 2].

It is concluded that almost the complete HCV genome has been cloned and sequenced by the procedures described above.

The 0.8 kb λgt11 nucleic acid sequence encoding an immunogenic HCV polypeptide identified with anti HCV serum was partially sequenced (see [SEQ ID NOS: 12 and 13] which revealed that this sequence is located within 1.2 and 2.0 kb on the HCV RNA.

EXAMPLE 3

Molecular Cloning and Expression of Fusion Proteins of HCV cDNA fragments derived from two regions of the HCV genome, i.e. the 0.8 kb λgt11 insert of example 1 encoding amino acids 262–546 (see [SEQ ID NOS: 1 and 2] and the nucleic acid sequence encoding amino acids 747–1071 ([SEQ ID NOS: 1 and 2]), are expressed as fusion proteins in the pEx system (Strebel, K. et al., 1986).

Bacterial extracts were separated by SDS-PAGE and stained according to standard procedures, and then tested for reactivity with the goat anti-HCV serum of example 1 in a Western blot.

The HCV specific fusion proteins were partially purified by SDS-PAGE and transfered to nitrocellulose and incubated with the goat anti-HCV serum. Specific antibodies against said fusion proteins were obtained after elution.

Antibodies specific for the above-mentioned fusion proteins were employed in a radio-immuno precipitation assay.

Results

Both fusion proteins expressed in the pEx system were clearly identified as HCV specific after reaction with the goat anti-HCV serum.

Monospecific antiserum prepared against both fusions proteins precipitated HCV glycoproteins.

Antibodies specific for the 262–546-fusion protein precipitated the 44/48 kD and 33 kD protein, antibodies specific for the 747–1071-fusion protein precipitated the 55 kD protein from virus infected cells.

EXAMPLE 4

Molecular Cloning and Expression of Structural Proteins Via Vaccinia Virus

A fragment of the 4,0 kb clone shown in FIG. 1 (pHCK11) is prepared starting at the HinfI restriction site (nucleotide 372) and ending at an artificial EcoRI site (nucleotide 4000) (Maniatis et al. 1982). For the 5' end an oligonucleotide adaptor was synthesized which contained an overhang compatible to BamHI, the original ATG(364–366) as translational start codon and a protruding end compatible to HinfI at the 3' end (SEQ ID NO: 5 and 6).

| 5' GATCCACCATGGAGTT | HinfI |
|---|---|
| BamHI    GTGGTACCTCAACTTA | 5' |

At the 3' end of the construct a translational stop codon was introduced by deletion of the EcoRI protruding end with Mung bean nuclease and ligation into a blunt-end StuI/EcoRI adaptor residue (SEQ ID NO: 7):

| 5' GCCTGAATTC | 3' EcoRI |
|---|---|
| CGGACTTAAG | |

(Maniatis et al. 1982).

Prior to inserting above-mentioned HCV sequences into vaccinia virus the heterologous gene is cloned into a recombination vector. For this purpose a pGS62 plasmid (Cranage, M. P. et al. 1986) was used which contains a cloning site downstream the P7.5K promotor within the 4.9 kb thymidine kinase sequence. The cloning site comprises three unique restriction sites, BamHI, SmaI and EcoRI. The recombination vector pGS62-3.8 was established by ligation of the described HCV sequence (372–4000) together with the adaptors into the BamHI/EcoRI digested pGS62.

Figure 2:
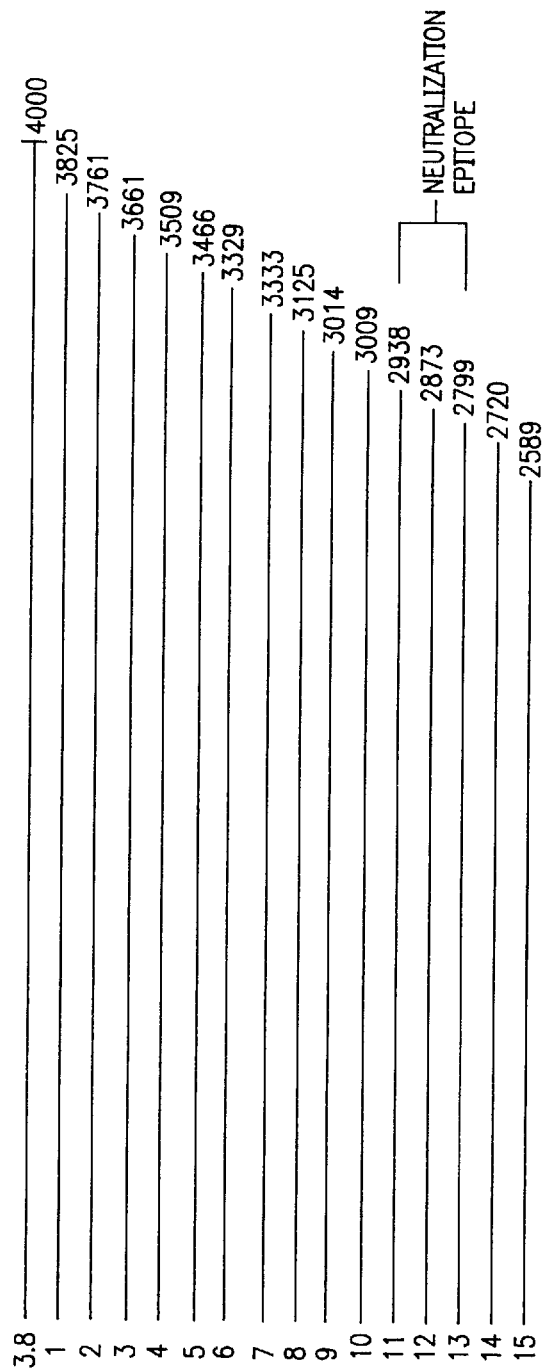

Based on the plasmid a set of 15 deletion mutants was established. By treatment with ExonucleaseIII (Hennikof et al., 1987) subsequent shortening of the HCV cDNA from the 3' end was performed. All deletions are located within the region coding for the HCV 55 kD protein by removal of about 100 bp; most of the 55 kD protein is lost in mutant 15 ending at nucleotide 2589. ExoIII shortened cDNA clones were ligated into the pGS62 giving rise to pGS62-3.8Exo 1–15 (FIG. 2).

CVI cells were infected with vaccinia (strain Copenhagen, mutant TS7) at a MOI of 0.1. Three hours after infection pGS62-3.8 DNA as well as vaccinia WR DNA were transfected by the $Ca_3(PO_4)_2$ precipitation method and incubated for two days. Virus progeny was harvested and selected for tk-phenotype on 143 tk-cells in the presence of brom-deoxy-Uridine (100 µg/ml). This selection was performed at least twice followed by two further cycles of plaque purification.

Characterization of vaccinia-HCV recombinants

CVI cells were infected at an MOI between 2 and 10 with vaccinia-HCV recombinants and incubated for 8–16 hours. After fixation of the cells indirect immuno-fluorescence was performed using either monoclonal antibodies specific for HCV 55 kD protein or polyvalent anti-HCV sera. In all cases a cytoplasmatic fluorescence could be demonstrated.

After radioimmunoprecipitation and western blot analysis of cells infected with vaccinia recombinants four HCV-specific proteins were detected. By labeling with [$^3$H] glucosamine it was shown that three of these proteins are glycosylated. The apparent molecular weights of these proteins were identical to those found in HCV infected cells with HCV specific sera, namely 20 kD (core), 44/48 kD, 33 kD and 55 kD.

Proteolytic processing and modifications appear to be authentic since HCV proteins produced by expression via vaccinia virus have the same apparent molecular weights as in HCV infected cells.

Induction of neutralizing antibodies against HCV in mice.

Four groups of mice (3 mice/group) were infected once with

| a. Vaccinia WR wildtype | ($5 \times 10^6$ pfu/individual) | WR |
|---|---|---|
| b. Vaccinia 3.8 recombinant | ($5 \times 10^7$ pfu/individual) | VAC3.8 |
| c. Vaccinia 3.8Exo 4 | ($5 \times 10^7$ pfu/individual) | VAC3.8Exo 4 |
| (55 kD deleted) | ($5 \times 10^7$ pfu/individual) | VAC3.8Exo 5 |
| d. vaccinia 3.8Exo 5 | | |
| e. Vaccinia 3.8Exo 15 | ($5 \times 10^7$ pfu/individual) | VAC3.8Exo 15 |
| (55 kD deleted) | | | by injection of purified virus intraperitoneally. Mice were bled three weeks later. The reactivity of the sera was checked in a virus neutralization assay with HCV (Alfort) on PK[15] cells after serial dilution. (Rümenapf, T. et al. 1989).

Neutralization titers

| a. WR | <1:2 |
|---|---|
| b. VAC3.8 | 1:96 |
| c. VAC3.8Exo 4 | 1:96 |
| d. VAC3.8Exo 5 | <1:2 |
| e. VAC3.8Exo 15 | <1.2 |

From the above it can be concluded that vaccinia virus containing a nucleic acid sequence comprising the genetic information for all structural proteins (VAC3.8) is able to induce virus neutralizing antibodies in mice, while incomplete constructs VAC3.8Exo 5–15 and WR are not.

As all deletions are located within the region coding for HCV 55 kD protein (most of the 55 kD protein is lost in mutant 15 ending at nucleotide 2589) and the other structural proteins are still being expressed by the recombinant vaccinia virus, it is clear that the 55 kD protein is responsible for the induction of HCV neutralizing antibodies.

EXAMPLE 5

Immunization of Pigs with VAC3.8

Out of three piglets (about 20 kg in weight) one animal (no. 28) was infected with wild type vaccinia virus (WR strain) and the other two (no. 26, 27) with recombinant VAC3.8 (i.p., i.v. and i.d., respectively). For infection $1 \times 10^8$ pfu of vaccinia virus is applied to each animal.

Clinical signs in the course of vaccinia infection were apparent as erythema at the side of scarification and fever (41° C.) at day six after infection.

Titers against vaccinia and hog cholera virus:

Three weeks after infection the reactivity of the respective sera against vaccinia (WR on CVI cells) and HCV (Alfort on PK15 cells) was checked.

Neutralization was assayed after serial dilution of the sera by checking for complete absence of cpe (vaccinia) or specific signals in immunofluorescence (HCV). (Rümenapf, T. et al. 1989).

Neutralization titers against vaccinia:

| pig 28 (WR) | 1:8 |
| pig 26 (VAC3.8) | 1:16 |
| pig 27 (VAC3.8) | 1:16 |

Neutralization titers against HCV:

| pig 28 (WR) | <1:2 |
| pig 26 (VAC3.8) | 1:32 |
| pig 27 (VAC3.8) | 1:16 |

Challenge with HCV:

Four weeks after immunization with vaccinia each of the pigs was challenged by infection with $5 \times 10^7$ TCID$_{50}$ HCV Alfort. Virus was applicated oronasal according to the natural route of infection. This amount of virus has been experimentally determined to be compulsory lethal for pigs.

On day five after the challenge infection pig 28 revealed fever of 41.5° C. and kept this temperature until day 12. The moribund animal was killed that day expressing typical clinical signs of acute hog cholera.

Both pigs (26, 27) immunized with VAC3.8 did not show any sign of illness after the challenge with HCV for more than 14 days.

EXAMPLE 6

Construction of a 55 kD Protein Expression Vector

A. PRV vector.

Clone pHCK11 is digested with restriction enzymes SacI and HpaI according to standard techniques.

The resulting 1.3 kb fragment, located between nucleotides 2672 (AGCTC) and 3971 (GTT) comprising most of HCV 55 kD protein, is isolated and cloned into the pseudorabies virus (PRV) gX gene (Maniatis et al. 1982).

Briefly, the cloned gX sequence was digested with SacI and ApaI. The ApaI 5' protruding ends were made blunt by filling up with Klenow fragment. After ligation the putative gX leader peptide coding sequence was located just upstream of the inserted HCV 55 kD sequence.

A translational stop codon downstream the HCV sequence was introduced by digestion with Bgl II (Bgl II site: 3936–3941) and religation after filling up the overhangs with Klenow fragment. This construct was placed downstream of the PRV gX promotor (clone 16/4-1.3). Clone 16/4-1.3 was transfected into MDBK cells by the DEAE dextran method (Maniatis et al. 1989). 16 h. later cells were infected with PRV (m.o.i.=1). 4 h. post infection cells were fixed with a mixture of cold (−20° C.) methanol/acetone. Indirect immunofluorescence with monoclonal antibodies (MABs) anti-HCV 55 kD protein revealed a specific signal in 5–10% of the cells. PRV infected cells without transfection and cells only transfected with clone 16/4-1.3 did not show any signal in this assay.

B. Vaccinia vector.

Clone pHCK11 is digested with restriction enzymes NheI and HpaI according to standard techniques. NheI 5' protruding end was made blunt by treatment with mung bean nuclease. The resulting 1.5 kb fragment, located between nucleotides 2438 (C) and 3971 (GTT) comprising HCV 55 kD protein, is isolated and cloned into the pseudorabies virus (PRV) gx gene (Maniatis et al., 1989).

The cloned gx sequence was digested with SacI and ApaI. SacI and ApaI 3' protruding ends were made blunt by exonuclease treatment with Klenow fragment. After ligation the putative gx leader peptide coding sequence was located upstream of the inserted HCV 55 kD sequence.

A translational stop codon downstream the HCV sequence was introduced by digestion with BglII (BglII site 3936–3941) and religation after filling up the overhangs with Klenow fragment. This construct was isolated by digestion with estriction enzymes AviII and ScaI. Vaccinia recombination plasmid pGS62A (Cranage et al.; 1986) is digested with SmaI. The HCV coding sequence with gx leader sequence is ligated into the SmaI site of pGS62A. CVI-cells were infected with wild type Vaccinia strain WR and transfected with pGS62A containing gp 55 coding sequences. (Macket et al., 1984) Recombinant Vaccinia viruses expressing HCV gp55 were isolated.

Metabolic labeling of CVI cells infected with the Vaccinia recombinant virus containing the HCV gp55 gene was performed. HCV gp55 was detected after radio-immuno precipitation with HCV neutralizing monoclonal antibodies, SDS-PAGE and fluorography. Under nonreducing conditions for SDS-PAGE, the disulfide linked HCV gp55 homodimer (apparent molecular weight of about 100 kD) was observed. The migration characteristics were the same as for HCV gp55 precipitated from HCV infected cells.

EXAMPLE 7

Construction of a 44/48 kD Protein Expression Vector

Clone pHCK11 is digested with restriction enzymes BglI and BanI according to standard techniques. The resulting 0.7 kb fragment, located between nucleotide 1115 (TGTTGGC) and 1838 (GTGC) comprising the HCV 44/48 kD protein, is isolated and ligated to synthetic adaptors connecting the 5'BglI restriction site with the BamHI site of the vaccinia recombination vector pGS62A and the 3' BanI site with the EcoRI site of the vaccinia recombination vector. The sequence of the 5'adaptor is (SEQ ID NO: 8 and 9).

5'-GATCCACCATGGGGGCCCTGT-3' GTGGTAC-CCCCGGG

The sequence of the 3'adaptor is (SEQ ID NO: 10 and 11)
5'-GTGCCTATGCCTGAG-3' GATACGGACTCTTAA CVI-cells were infected with wild type Vaccinia strain WR and transfected with pGS62A containing the gp 44/48 coding sequences. Recombinant Vaccinia viruses expressing HCV gp 44/48 were isolated.

Metabolic labeling of CVI cells infected with the Vaccinia recombinant virus containing the HCV gp 44/48 gene was performed. HCV gp 44/48 was detected after radio-immuno precipitation with monoclonal antibodies, SDS-PAGE and fluorography. Under nonreducing conditions for SDS-PAGE, the disulfide linked HCV gp 44/48 homodimer (apparent molecular weight of about 100 kD) was observed. The migration characteristics were the same as for HCV gp 44/48 precipitated from HCV infected cells. It was demonstrated that the monoclonal antibodies which precipitated gp 44/48 from cells infected with the Vaccinia recombinant neutralize HCV.

BRIEF DESCRIPTION OF THE DRAWINGS

FIG. 1 displays physical maps of different HCV derived cDNA clones and their position relative to the RNA genome (upper line). Two HCV derived cDNA clones isolated after screening with either the antibody probe (0.8 kb clone) or the degenerated oligonucleotide probe (0.75 kb clone) are shown in the second line. The cDNA fragments chosen for nucleotide sequencing are indicated below. All numbers represent sizes of DNA fragments in kb. Restriction sites: B=Bgl II; E=EcoRI; H=Hind III; K=Kpn I; S=Sal I; Sm=Sma I.

FIG. 2 shows the length of the HCV DNA cloned in the pGS62 vector. A set of 15 deletion mutants derived from cDNA clone pHCK11 was established by treatment with Exonuclease III and cloned in the pGS62 vector giving rise to pGS62-3.8Exo 1–15. 3' end nucleotides are indicated.

REFERENCES

BENTON, W., and DAVIS, R. (1977). Screening λgt recombinant clones by hybridization to single plaques in sity. Science 196, 180–182.

CHIRGWIN, J. M., PRZYBYLA, A. E., MAcDONALD, R. J., and RUTTER, W. J. (1979). Isolation of biologically active ribonucleic acid from sources enriched in ribonuclease, Biochemistry 18, 5294–5299.

CRANAGE, M. P. et al. (1986). EMBO, J. 5, 3057–3063.

DAVIS, L. G., DIBNER, M. D., and BATTEY, J. F. (1986). Basic Methods in Molecular Biology, 190–191. Elsevier, New York, Amsterdam, London.

DENTE, L., SOLLAZZO, M., BALDARI, C., CESARENI, G., and CORTESE, R. (1985). The pEMBL family of single-stranded vectors. In: DNA Cloning, Vol. 1, (Glover, D. M., ed.), IRL Press Oxford/Washington DC, pp. 101–107.

GEYSEN et al., H. M. (1987) J. Immunol. Meth. 102, 259–274.

HENNIKOFF, S. (1987). Unidirectional digestion with exonuclease III in DNA sequence analysis. In: Meth. Enzymol. (Wu, R., ed.) 155, 156–165.

HUYNH, T. V., YOUNG, R. A., and DAVIS, R. W. (1985). Constructing and screening cDNA libraries in λgt10 and λgt11. In: DNA Cloning: A Practical Approach, Vol. 2, (Glover, D. M., ed.), IRL Press Oxford, pp. 49–78.

KEIL, G. M., EBELING-KEIL, A., and KOSZINOWSKI, U. H. (1984). Temporal regulation of murine cytomegalovirus transcription and mapping of viral RNA synthesized at immediate early times after infection, J. Virol. 50, 784–795.

MACKETT, M. et al. (1984) J. Virol. 49, 857–864.

MANIATIS, T., FRITSCH, E. F., and SAMBROOKS, S. (1982). Molecular Cloning, a Laboratory Manual. Cold Spring Harbor Laboratory Press, Cold Spring Harbor, N.Y.

SANGER, F., NICKLEN, S., and COULSON, A. R. (1977). DNA sequencing with chain-terminating inhibitors. Proc. Natl. Acad. Sci. U.S.A. 74, 5363–5467.

MANIATIS, T. et al. (1989). Molecular Cloning, a Laboratory Manual, second edition, Cold Spring Harbor Laboratory Press, Cold Spring Harbor, N.Y.

STREBEL, K. et al. (1986). J. Virology 57, 983–991.

RüMENOPF, T. et al. (1989). Virology 171, 18–27.

YOUNG, R. A., and DAVIS, R. W. (1983). Efficient isolation of genes by using antibody probes. Proc. Natl. Acad. Sci. U.S.A. 80, 1194–1198.

What is claimed is:

1. An isolated DNA sequence which encodes the 44/48 kD protein of hog cholera virus (HCV).

2. The DNA according to claim 1, which encodes a polypeptide comprising the amino acid sequence from about 263 to about 487 of SEQ ID NO:2.

3. The DNA according to claim 1, which comprises the DNA sequence from about 1150 to about 1824 of SEQ ID NO:1.

4. A recombinant nucleic acid molecule comprising a vector nucleic acid molecule and a DNA sequence according to claim 1.

5. The recombinant nucleic acid molecule acid according to claim 4, wherein the DNA sequence is operably linked to expression control sequences.

6. A host cell comprising the recombinant nucleic acid molecule according to claim 4.

7. A host cell according to claim 6, wherein the host cell is a virus or bacterium.

8. A host cell according to claim 7, wherein the virus is pseudorabies virus or vaccinia.

9. A vaccine for the protection of animals against hog cholera virus infection, comprising a host cell according to claim 4.

10. A method for the preparation of a hog cholera virus vaccine, comprising growing a host cell according to claim 6 in culture, harvesting the cells and mixing the cells with a pharmaceutically acceptable carrier.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 12284 base pairs
( B ) TYPE: nucleic acid
( C ) STRANDEDNESS: double
( D ) TOPOLOGY: linear ( i i ) MOLECULE TYPE: cDNA ( v i ) ORIGINAL SOURCE:
( A ) ORGANISM: Hog cholera virus
( B ) STRAIN: Alfort
( H ) CELL LINE: PK 15 and 38A1D ( i x ) FEATURE:
( A ) NAME/KEY: CDS -continued ( B ) LOCATION: 364..12060
    ( D ) OTHER INFORMATION: /label= 435_kDA_protein ( i x ) FEATURE:
    ( A ) NAME/KEY: primer_bind
    ( B ) LOCATION: complement (2587..2619)
    ( D ) OTHER INFORMATION: /label= primer_1

( i x ) FEATURE:
    ( A ) NAME/KEY: primer_bind
    ( B ) LOCATION: complement (2842..2880)
    ( D ) OTHER INFORMATION: /label= primer_2

( i x ) FEATURE:
    ( A ) NAME/KEY: variation
    ( B ) LOCATION: replace(127, "c")

( i x ) FEATURE:
    ( A ) NAME/KEY: variation
    ( B ) LOCATION: replace(1522, "g")

( i x ) FEATURE:
    ( A ) NAME/KEY: variation
    ( B ) LOCATION: replace(10989, "t")

( x i ) SEQUENCE DESCRIPTION: SEQ ID NO:1:

```
GTTAGCTCTT  TCTCGTATAC  GATATTGGAT  ACACTAAATT  TCGATTTGGT  CTAGGGCACC       60

CCTCCAGCGA  CGGCCGAAAT  GGGCTAGCCA  TGCCCATAGT  AGGACTAGCA  AACGGAGGGA      120

CTAGCCGTAG  TGGCGAGCTC  CCTGGGTGGT  CTAAGTCCTG  AGTACAGGAC  AGTCGTCAGT      180

AGTTCGACGT  GAGCACTAGC  CCACCTCGAG  ATGCTACGTG  GACGAGGGCA  TGCCCAAGAC      240

ACACCTTAAC  CCTGGCGGGG  GTCGCTAGGG  TGAAATCACA  TTATGTGATG  GGGGTACGAC      300

CTGATAGGGT  GCTGCAGAGG  CCCACTAGCA  GGCTAGTATA  AAAATCTCTG  CTGTACATGG      360
```

```
CAC ATG GAG TTG AAT CAT TTT GAA TTA TTA TAC AAA ACA AGC AAA CAA           408
    Met Glu Leu Asn His Phe Glu Leu Leu Tyr Lys Thr Ser Lys Gln
     1               5                  10                  15

AAA CCA GTG GGA GTG GAG GAA CCG GTG TAT GAC ACC GCG GGG AGA CCA           456
Lys Pro Val Gly Val Glu Glu Pro Val Tyr Asp Thr Ala Gly Arg Pro
            20                  25                  30

CTA TTT GGG AAC CCA AGT GAG GTA CAC CCA CAA TCA ACG CTG AAG CTG           504
Leu Phe Gly Asn Pro Ser Glu Val His Pro Gln Ser Thr Leu Lys Leu
                35                  40                  45

CCA CAC GAC AGG GGG AGA GGA GAT ATC AGA ACA ACA CTG AGG GAC CTA           552
Pro His Asp Arg Gly Arg Gly Asp Ile Arg Thr Thr Leu Arg Asp Leu
        50                  55                  60

CCC AGG AAA GGT GAC TGT AGG AGT GGC AAC CAT CTA GGC CCG GTT AGT           600
Pro Arg Lys Gly Asp Cys Arg Ser Gly Asn His Leu Gly Pro Val Ser
    65                  70                  75

GGG ATA TAC ATA AAG CCC GGC CCT GTC TAC TAT CAG GAC TAC ACG GGC           648
Gly Ile Tyr Ile Lys Pro Gly Pro Val Tyr Tyr Gln Asp Tyr Thr Gly
80                  85                  90                  95

CCA GTC TAT CAC AGA GCT CCT TTA GAG TTC TTT GAT GAG GCC CAG TTC           696
Pro Val Tyr His Arg Ala Pro Leu Glu Phe Phe Asp Glu Ala Gln Phe
            100                 105                 110

TGC GAG GTG ACT AAG AGA ATA GGC AGG GTC ACG GGT AGT GAT GGT AAG           744
Cys Glu Val Thr Lys Arg Ile Gly Arg Val Thr Gly Ser Asp Gly Lys
                115                 120                 125

CTT TAC CAC ATA TAT GTG TGC GTC GAT GGT TGC ATA CTG CTG AAA TTA           792
Leu Tyr His Ile Tyr Val Cys Val Asp Gly Cys Ile Leu Leu Lys Leu
        130                 135                 140

GCC AAA AGG GGC ACA CCC AGA ACC CTA AAG TGG ATT AGG AAC TTC ACC           840
Ala Lys Arg Gly Thr Pro Arg Thr Leu Lys Trp Ile Arg Asn Phe Thr
    145                 150                 155

AAC TGT CCA TTA TGG GTA ACC AGT TGC TCC GAT GAC GGC GCA AGT GGC           888
```

```
Asn Cys Pro Leu Trp Val Thr Ser Cys Ser Asp Asp Gly Ala Ser Gly
160             165             170             175

AGC AAG GAT AAG AAG CCA GAC AGA ATG AAC AAA GGT AAG TTG AAG ATA    936
Ser Lys Asp Lys Lys Pro Asp Arg Met Asn Lys Gly Lys Leu Lys Ile
                180             185             190

GCC CCA AGA GAG CAT GAG AAG GAC AGC AAG ACC AAG CCT CCT GAT GCA    984
Ala Pro Arg Glu His Glu Lys Asp Ser Lys Thr Lys Pro Pro Asp Ala
            195             200             205

ACG ATT GTA GTA GAG GGA GTA AAA TAC CAA ATC AAA AAG AAA GGC AAA   1032
Thr Ile Val Val Glu Gly Val Lys Tyr Gln Ile Lys Lys Lys Gly Lys
        210             215             220

GTC AAA GGG AAG AAC ACA CAA GAC GGC CTG TAC CAT AAT AAG AAC AAG   1080
Val Lys Gly Lys Asn Thr Gln Asp Gly Leu Tyr His Asn Lys Asn Lys
    225             230             235

CCA CCA GAG TCC AGG AAG AAA CTA GAA AAA GCC CTG TTG GCT TGG GCG   1128
Pro Pro Glu Ser Arg Lys Lys Leu Glu Lys Ala Leu Leu Ala Trp Ala
240             245             250             255

GTG ATA ACA ATC TTG CTG TAC CAG CCT GTA GCA GCC GAG AAC ATA ACT   1176
Val Ile Thr Ile Leu Leu Tyr Gln Pro Val Ala Ala Glu Asn Ile Thr
                260             265             270

CAA TGG AAC CTG AGT GAC AAC GGC ACT AAT GGT ATT CAG CGA GCC ATG   1224
Gln Trp Asn Leu Ser Asp Asn Gly Thr Asn Gly Ile Gln Arg Ala Met
            275             280             285

TAT CTT AGA GGG GTT AAC AGG AGC TTA CAT GGG ATC TGG CCC GAG AAA   1272
Tyr Leu Arg Gly Val Asn Arg Ser Leu His Gly Ile Trp Pro Glu Lys
        290             295             300

ATA TGC AAG GGG GTC CCC ACT CAT CTG GCC ACT GAC ACG GAA CTG AAA   1320
Ile Cys Lys Gly Val Pro Thr His Leu Ala Thr Asp Thr Glu Leu Lys
    305             310             315

GAG ATA CGC GGG ATG ATG GAT GCC AGC GAG AGG ACA AAC TAT ACG TGC   1368
Glu Ile Arg Gly Met Met Asp Ala Ser Glu Arg Thr Asn Tyr Thr Cys
320             325             330             335

TGT AGG TTA CAA AGA CAT GAA TGG AAC AAA CAT GGA TGG TGT AAC TGG   1416
Cys Arg Leu Gln Arg His Glu Trp Asn Lys His Gly Trp Cys Asn Trp
                340             345             350

TAC AAC ATA GAC CCT TGG ATT CAG TTA ATG AAC AGG ACC CAA ACA AAT   1464
Tyr Asn Ile Asp Pro Trp Ile Gln Leu Met Asn Arg Thr Gln Thr Asn
            355             360             365

TTG ACA GAA GGC CCT CCA GAT AAG GAG TGT GCC GTG ACC TGC AGG TAT   1512
Leu Thr Glu Gly Pro Pro Asp Lys Glu Cys Ala Val Thr Cys Arg Tyr
        370             375             380

GAC AAA AAT ACC GAT GTC AAC GTG GTC ACC CAG GCC AGG AAT AGG CCA   1560
Asp Lys Asn Thr Asp Val Asn Val Val Thr Gln Ala Arg Asn Arg Pro
    385             390             395

ACT ACT CTG ACT GGC TGC AAG AAA GGG AAA AAC TTT TCA TTC GCA GGC   1608
Thr Thr Leu Thr Gly Cys Lys Lys Gly Lys Asn Phe Ser Phe Ala Gly
400             405             410             415

ACA GTC ATA GAG GGC CCG TGC AAT TTC AAC GTT TCC GTG GAG GAC ATC   1656
Thr Val Ile Glu Gly Pro Cys Asn Phe Asn Val Ser Val Glu Asp Ile
                420             425             430

TTA TAC GGA GAC CAT GAG TGT GGC AGT CTG CTC CAG GAC ACG GCT CTG   1704
Leu Tyr Gly Asp His Glu Cys Gly Ser Leu Leu Gln Asp Thr Ala Leu
            435             440             445

TAC CTA TTG GAT GGA ATG ACC AAC ACT ATA GAG AAT GCC AGG CAA GGT   1752
Tyr Leu Leu Asp Gly Met Thr Asn Thr Ile Glu Asn Ala Arg Gln Gly
        450             455             460

GCG GCG CGG GTG ACA TCT TGG CTT GGG AGG CAG CTC AGT ACC GCA GGG   1800
Ala Ala Arg Val Thr Ser Trp Leu Gly Arg Gln Leu Ser Thr Ala Gly
    465             470             475

AAG AAG CTA GAG AGG AGA AGC AAA ACC TGG TTT GGT GCC TAT GCC CTG   1848
```

| | | | | | | | | | | | | | | | | |
|---|---|---|---|---|---|---|---|---|---|---|---|---|---|---|---|---|
| Lys<br>480 | Lys | Leu | Glu | Arg | Arg<br>485 | Ser | Lys | Thr | Trp | Phe<br>490 | Gly | Ala | Tyr | Ala | Leu<br>495 | |
| TCA<br>Ser | CCT<br>Pro | TAC<br>Tyr | TGC<br>Cys | AAT<br>Asn<br>500 | GTG<br>Val | ACT<br>Thr | AGA<br>Arg | AAA<br>Lys | ATA<br>Ile<br>505 | GGG<br>Gly | TAC<br>Tyr | ATA<br>Ile | TGG<br>Trp | TAT<br>Tyr<br>510 | ACA<br>Thr | 1896 |
| AAC<br>Asn | AAC<br>Asn | TGC<br>Cys | ACC<br>Thr<br>515 | CCG<br>Pro | GCA<br>Ala | TGC<br>Cys | CTC<br>Leu | CCT<br>Pro<br>520 | AAG<br>Lys | AAC<br>Asn | ACA<br>Thr | AAA<br>Lys | ATA<br>Ile<br>525 | ATA<br>Ile | GGC<br>Gly | 1944 |
| CCT<br>Pro | GGA<br>Gly | AAG<br>Lys<br>530 | TTT<br>Phe | GAC<br>Asp | ACC<br>Thr | AAT<br>Asn | GCG<br>Ala<br>535 | GAA<br>Glu | GAC<br>Asp | GGG<br>Gly | AAG<br>Lys | ATC<br>Ile<br>540 | CTT<br>Leu | CAT<br>His | GAA<br>Glu | 1992 |
| ATG<br>Met | GGG<br>Gly<br>545 | GGC<br>Gly | CAC<br>His | CTA<br>Leu | TCA<br>Ser | GAA<br>Glu<br>550 | TTT<br>Phe | TTG<br>Leu | TTG<br>Leu | CTT<br>Leu | TCT<br>Ser<br>555 | CTA<br>Leu | GTT<br>Val | ATC<br>Ile | CTG<br>Leu | 2040 |
| TCT<br>Ser<br>560 | GAC<br>Asp | TTT<br>Phe | GCC<br>Ala | CCC<br>Pro | GAG<br>Glu<br>565 | ACA<br>Thr | GCT<br>Ala | AGC<br>Ser | ACG<br>Thr | CTA<br>Leu<br>570 | TAC<br>Tyr | CTA<br>Leu | ATT<br>Ile | TTA<br>Leu | CAC<br>His<br>575 | 2088 |
| TAT<br>Tyr | GCA<br>Ala | ATC<br>Ile | CCC<br>Pro | CAG<br>Gln<br>580 | TCC<br>Ser | CAC<br>His | GAA<br>Glu | GAA<br>Glu | CCT<br>Pro<br>585 | GAA<br>Glu | GGT<br>Gly | TGT<br>Cys | GAT<br>Asp | ACG<br>Thr<br>590 | AAC<br>Asn | 2136 |
| CAA<br>Gln | CTT<br>Leu | AAC<br>Asn | CTA<br>Leu<br>595 | ACA<br>Thr | GTG<br>Val | AAA<br>Lys | CTT<br>Leu | AGG<br>Arg<br>600 | ACA<br>Thr | GAA<br>Glu | GAC<br>Asp | GTA<br>Val | GTG<br>Val<br>605 | CCA<br>Pro | TCA<br>Ser | 2184 |
| TCA<br>Ser | GTT<br>Val | TGG<br>Trp<br>610 | AAT<br>Asn | ATT<br>Ile | GGC<br>Gly | AAA<br>Lys | TAT<br>Tyr<br>615 | GTT<br>Val | TGT<br>Cys | GTT<br>Val | AGA<br>Arg | CCA<br>Pro<br>620 | GAC<br>Asp | TGG<br>Trp | TGG<br>Trp | 2232 |
| CCG<br>Pro | TAT<br>Tyr<br>625 | GAA<br>Glu | ACT<br>Thr | AAA<br>Lys | GTG<br>Val | GCT<br>Ala<br>630 | CTG<br>Leu | CTG<br>Leu | TTT<br>Phe | GAA<br>Glu | GAG<br>Glu<br>635 | GCA<br>Ala | GGA<br>Gly | CAG<br>Gln | GTT<br>Val | 2280 |
| ATA<br>Ile<br>640 | AAG<br>Lys | CTA<br>Leu | GTC<br>Val | CTA<br>Leu | CGG<br>Arg<br>645 | GCA<br>Ala | CTG<br>Leu | AGG<br>Arg | GAT<br>Asp | TTA<br>Leu<br>650 | ACT<br>Thr | AGG<br>Arg | GTC<br>Val | TGG<br>Trp | AAC<br>Asn<br>655 | 2328 |
| AGC<br>Ser | GCA<br>Ala | TCA<br>Ser | ACT<br>Thr | ACT<br>Thr<br>660 | GCG<br>Ala | TTT<br>Phe | CTC<br>Leu | ATT<br>Ile | TGC<br>Cys<br>665 | TTG<br>Leu | ATA<br>Ile | AAA<br>Lys | GTA<br>Val | TTG<br>Leu<br>670 | AGA<br>Arg | 2376 |
| GGA<br>Gly | CAG<br>Gln | GTT<br>Val | GTG<br>Val<br>675 | CAA<br>Gln | GGT<br>Gly | ATA<br>Ile | ATA<br>Ile | TGG<br>Trp<br>680 | CTG<br>Leu | CTG<br>Leu | CTG<br>Leu | GTG<br>Val | ACC<br>Thr<br>685 | GGG<br>Gly | GCA<br>Ala | 2424 |
| CAA<br>Gln | GGG<br>Gly | CGG<br>Arg<br>690 | CTA<br>Leu | GCC<br>Ala | TGT<br>Cys | AAG<br>Lys | GAA<br>Glu<br>695 | GAC<br>Asp | TAC<br>Tyr | AGG<br>Arg | TAT<br>Tyr | GCG<br>Ala<br>700 | ATC<br>Ile | TCG<br>Ser | TCA<br>Ser | 2472 |
| ACC<br>Thr | AAT<br>Asn<br>705 | GAG<br>Glu | ATA<br>Ile | GGG<br>Gly | CTG<br>Leu<br>710 | CTG<br>Leu | GGC<br>Gly | GCT<br>Ala | GAA<br>Glu | GGT<br>Gly<br>715 | CTC<br>Leu | ACC<br>Thr | ACT<br>Thr | ACC<br>Thr | TGG<br>Trp | 2520 |
| AAA<br>Lys<br>720 | GAA<br>Glu | TAC<br>Tyr | AGC<br>Ser | CAC<br>His | GGT<br>Gly<br>725 | TTG<br>Leu | CAG<br>Gln | CTG<br>Leu | GAC<br>Asp | GAC<br>Asp<br>730 | GGA<br>Gly | ACC<br>Thr | GTT<br>Val | AAG<br>Lys | GCC<br>Ala<br>735 | 2568 |
| GTC<br>Val | TGC<br>Cys | ACT<br>Thr | GCA<br>Ala | GGG<br>Gly<br>740 | TCC<br>Ser | TTT<br>Phe | AAA<br>Lys | GTC<br>Val | ACA<br>Thr<br>745 | GCA<br>Ala | CTT<br>Leu | AAC<br>Asn | GTG<br>Val | GTT<br>Val<br>750 | AGT<br>Ser | 2616 |
| AGG<br>Arg | AGG<br>Arg | TAT<br>Tyr | CTA<br>Leu<br>755 | GCA<br>Ala | TCA<br>Ser | TTG<br>Leu | CAC<br>His | AAG<br>Lys<br>760 | AGG<br>Arg | GCT<br>Ala | CTA<br>Leu | CCC<br>Pro | ACC<br>Thr<br>765 | TCA<br>Ser | GTG<br>Val | 2664 |
| ACA<br>Thr | TTT<br>Phe | GAG<br>Glu<br>770 | CTC<br>Leu | CTA<br>Leu | TTT<br>Phe | GAC<br>Asp | GGG<br>Gly<br>775 | ACC<br>Thr | AAC<br>Asn | CCA<br>Pro | GCA<br>Ala | ATC<br>Ile<br>780 | GAG<br>Glu | GAG<br>Glu | ATG<br>Met | 2712 |
| GAT<br>Asp | GAT<br>Asp<br>785 | GAC<br>Asp | TTC<br>Phe | GGA<br>Gly | TTT<br>Phe<br>790 | GGG<br>Gly | CTG<br>Leu | TGC<br>Cys | CCA<br>Pro | TTT<br>Phe<br>795 | GAC<br>Asp | ACG<br>Thr | AGT<br>Ser | CCT<br>Pro | GTG<br>Val | 2760 |
| ATC | AAA | GGG | AAG | TAC | AAC | ACC | ACT | TTG | TTA | AAC | GGC | AGT | GCT | TTC | TAT | 2808 |

|  |  |  |  |  |  |  |  |  |  |  |  |  |  |  |  |
|---|---|---|---|---|---|---|---|---|---|---|---|---|---|---|---|
| Ile | Lys | Gly | Lys | Tyr | Asn | Thr | Thr | Leu | Leu | Asn | Gly | Ser | Ala | Phe | Tyr |
| 800 |  |  |  |  | 805 |  |  |  | 810 |  |  |  |  |  | 815 |

| CTA | GTC | TGC | CCA | ATA | GGA | TGG | ACT | GGT | GTC | GTA | GAG | TGC | ACA | GCA | GTG | 2856 |
|---|---|---|---|---|---|---|---|---|---|---|---|---|---|---|---|---|
| Leu | Val | Cys | Pro | Ile | Gly | Trp | Thr | Gly | Val | Val | Glu | Cys | Thr | Ala | Val |  |
|  |  |  |  | 820 |  |  |  |  | 825 |  |  |  |  | 830 |  |  |

| AGC | CCC | ACA | ACC | TTG | AGA | ACA | GAA | GTG | GTG | AAA | ACC | TTC | AGG | AGA | GAT | 2904 |
|---|---|---|---|---|---|---|---|---|---|---|---|---|---|---|---|---|
| Ser | Pro | Thr | Thr | Leu | Arg | Thr | Glu | Val | Val | Lys | Thr | Phe | Arg | Arg | Asp |  |
|  |  |  | 835 |  |  |  |  | 840 |  |  |  |  | 845 |  |  |  |

| AAG | CCT | TTT | CCA | CAT | AGA | GTA | GAC | TGT | GTG | ACC | ACC | ATA | GTA | GAA | AAA | 2952 |
|---|---|---|---|---|---|---|---|---|---|---|---|---|---|---|---|---|
| Lys | Pro | Phe | Pro | His | Arg | Val | Asp | Cys | Val | Thr | Thr | Ile | Val | Glu | Lys |  |
|  |  | 850 |  |  |  |  | 855 |  |  |  |  | 860 |  |  |  |  |

| GAA | GAC | CTA | TTC | CAT | TGC | AAG | TTG | GGG | GGT | AAT | TGG | ACA | TGT | GTA | AAA | 3000 |
|---|---|---|---|---|---|---|---|---|---|---|---|---|---|---|---|---|
| Glu | Asp | Leu | Phe | His | Cys | Lys | Leu | Gly | Gly | Asn | Trp | Thr | Cys | Val | Lys |  |
|  | 865 |  |  |  |  | 870 |  |  |  |  | 875 |  |  |  |  |  |

| GGC | GAC | CCA | GTG | ACT | TAT | AAG | GGG | GGG | CAA | GTA | AAG | CAG | TGC | AGG | TGG | 3048 |
|---|---|---|---|---|---|---|---|---|---|---|---|---|---|---|---|---|
| Gly | Asp | Pro | Val | Thr | Tyr | Lys | Gly | Gly | Gln | Val | Lys | Gln | Cys | Arg | Trp |  |
| 880 |  |  |  |  | 885 |  |  |  |  | 890 |  |  |  |  | 895 |  |

| TGT | GGT | TTC | GAG | TTT | AAA | GAG | CCC | TAC | GGG | CTC | CCA | CAC | TAC | CCT | ATA | 3096 |
|---|---|---|---|---|---|---|---|---|---|---|---|---|---|---|---|---|
| Cys | Gly | Phe | Glu | Phe | Lys | Glu | Pro | Tyr | Gly | Leu | Pro | His | Tyr | Pro | Ile |  |
|  |  |  |  | 900 |  |  |  |  | 905 |  |  |  |  | 910 |  |  |

| GGC | AAG | TGC | ATC | CTA | ACA | AAT | GAG | ACA | GGT | TAC | AGG | GTA | GTA | GAT | TCC | 3144 |
|---|---|---|---|---|---|---|---|---|---|---|---|---|---|---|---|---|
| Gly | Lys | Cys | Ile | Leu | Thr | Asn | Glu | Thr | Gly | Tyr | Arg | Val | Val | Asp | Ser |  |
|  |  |  | 915 |  |  |  |  | 920 |  |  |  |  | 925 |  |  |  |

| ACA | GAC | TGC | AAC | AGA | GAT | GGC | GTC | GTT | ATT | AGC | ACT | GAA | GGG | GAA | CAT | 3192 |
|---|---|---|---|---|---|---|---|---|---|---|---|---|---|---|---|---|
| Thr | Asp | Cys | Asn | Arg | Asp | Gly | Val | Val | Ile | Ser | Thr | Glu | Gly | Glu | His |  |
|  |  | 930 |  |  |  |  | 935 |  |  |  |  | 940 |  |  |  |  |

| GAG | TGC | TTG | ATT | GGC | AAC | ACT | ACC | GTC | AAG | GTG | CAT | GCA | CTG | GAT | GAA | 3240 |
|---|---|---|---|---|---|---|---|---|---|---|---|---|---|---|---|---|
| Glu | Cys | Leu | Ile | Gly | Asn | Thr | Thr | Val | Lys | Val | His | Ala | Leu | Asp | Glu |  |
|  | 945 |  |  |  |  | 950 |  |  |  |  | 955 |  |  |  |  |  |

| AGA | TTG | GGC | CCT | ATG | CCG | TGC | AGA | CCC | AAA | GAA | ATC | GTC | TCT | AGT | GAG | 3288 |
|---|---|---|---|---|---|---|---|---|---|---|---|---|---|---|---|---|
| Arg | Leu | Gly | Pro | Met | Pro | Cys | Arg | Pro | Lys | Glu | Ile | Val | Ser | Ser | Glu |  |
| 960 |  |  |  |  | 965 |  |  |  |  | 970 |  |  |  |  | 975 |  |

| GGA | CCT | GTG | AGG | AAA | ACT | TCT | TGT | ACA | TTC | AAC | TAC | ACA | AAG | ACT | CTA | 3336 |
|---|---|---|---|---|---|---|---|---|---|---|---|---|---|---|---|---|
| Gly | Pro | Val | Arg | Lys | Thr | Ser | Cys | Thr | Phe | Asn | Tyr | Thr | Lys | Thr | Leu |  |
|  |  |  |  | 980 |  |  |  |  | 985 |  |  |  |  | 990 |  |  |

| AGA | AAC | AAA | TAC | TAT | GAG | CCC | AGA | GAC | AGT | TAC | TTC | CAG | CAA | TAT | ATG | 3384 |
|---|---|---|---|---|---|---|---|---|---|---|---|---|---|---|---|---|
| Arg | Asn | Lys | Tyr | Tyr | Glu | Pro | Arg | Asp | Ser | Tyr | Phe | Gln | Gln | Tyr | Met |  |
|  |  | 995 |  |  |  |  | 1000 |  |  |  |  | 1005 |  |  |  |  |

| CTC | AAG | GGC | GAG | TAT | CAA | TAC | TGG | TTT | AAT | CTG | GAC | GTG | ACC | GAC | CAC | 3432 |
|---|---|---|---|---|---|---|---|---|---|---|---|---|---|---|---|---|
| Leu | Lys | Gly | Glu | Tyr | Gln | Tyr | Trp | Phe | Asn | Leu | Asp | Val | Thr | Asp | His |  |
|  |  |  | 1010 |  |  |  |  | 1015 |  |  |  |  | 1020 |  |  |  |

| CAC | ACA | GAC | TAC | TTT | GCC | GAG | TTT | GTT | GTC | TTG | GTA | GTA | GTA | GCA | CTG | 3480 |
|---|---|---|---|---|---|---|---|---|---|---|---|---|---|---|---|---|
| His | Thr | Asp | Tyr | Phe | Ala | Glu | Phe | Val | Val | Leu | Val | Val | Val | Ala | Leu |  |
|  |  |  | 1025 |  |  |  |  | 1030 |  |  |  |  | 1035 |  |  |  |

| TTA | GGA | GGA | AGG | TAC | GTT | CTG | TGG | CTA | ATA | GTG | ACC | TAC | ATA | ATT | CTA | 3528 |
|---|---|---|---|---|---|---|---|---|---|---|---|---|---|---|---|---|
| Leu | Gly | Gly | Arg | Tyr | Val | Leu | Trp | Leu | Ile | Val | Thr | Tyr | Ile | Ile | Leu |  |
| 1040 |  |  |  |  | 1045 |  |  |  |  | 1050 |  |  |  |  | 1055 |  |

| ACA | GAG | CAG | CTC | GCT | GCT | GGT | CTA | CAG | CTA | GGC | CAG | GGT | GAG | GTG | GTA | 3576 |
|---|---|---|---|---|---|---|---|---|---|---|---|---|---|---|---|---|
| Thr | Glu | Gln | Leu | Ala | Ala | Gly | Leu | Gln | Leu | Gly | Gln | Gly | Glu | Val | Val |  |
|  |  |  |  |  | 1060 |  |  |  |  | 1065 |  |  |  |  | 1070 |  |

| TTG | ATA | GGG | AAC | CTA | ATT | ACC | CAC | ACG | GAC | AAT | GAG | GTG | GTG | GTG | TAC | 3624 |
|---|---|---|---|---|---|---|---|---|---|---|---|---|---|---|---|---|
| Leu | Ile | Gly | Asn | Leu | Ile | Thr | His | Thr | Asp | Asn | Glu | Val | Val | Val | Tyr |  |
|  |  |  |  | 1075 |  |  |  |  | 1080 |  |  |  |  | 1085 |  |  |

| TTC | CTA | CTG | CTC | TAC | TTA | GTA | ATA | AGA | GAT | GAG | CCC | ATA | AAG | AAA | TGG | 3672 |
|---|---|---|---|---|---|---|---|---|---|---|---|---|---|---|---|---|
| Phe | Leu | Leu | Leu | Tyr | Leu | Val | Ile | Arg | Asp | Glu | Pro | Ile | Lys | Lys | Trp |  |
|  |  |  | 1090 |  |  |  |  | 1095 |  |  |  |  | 1100 |  |  |  |

| ATA | CTA | CTG | CTG | TTT | CAT | GCA | ATG | ACT | AAC | AAT | CCA | GTC | AAG | ACC | ATA | 3720 |
|---|---|---|---|---|---|---|---|---|---|---|---|---|---|---|---|---|
| Ile | Leu | Leu | Leu | Phe | His | Ala | Met | Thr | Asn | Asn | Pro | Val | Lys | Thr | Ile |  |
|  | 1105 |  |  |  |  | 1110 |  |  |  |  | 1115 |  |  |  |  |  |

| ACA | GTA | GCA | TTG | CTA | ATG | ATC | AGT | GGG | GTT | GCC | AAG | GGT | GGT | AAG | ATA | 3768 |

```
Thr Val Ala Leu Leu Met Ile Ser Gly Val Ala Lys Gly Gly Lys Ile
1120                1125                1130                1135

GAT GGT GGC TGG CAG AGA CAA CCG GTG ACC AGT TTT GAC ATC CAA CTC    3816
Asp Gly Gly Trp Gln Arg Gln Pro Val Thr Ser Phe Asp Ile Gln Leu
                    1140                1145                1150

GCA CTG GCA GTC GTA GTA GTC GTT GTG ATG TTG CTG GCA AAG AGA GAC    3864
Ala Leu Ala Val Val Val Val Val Val Met Leu Leu Ala Lys Arg Asp
                1155                1160                1165

CCG ACT ACT TTC CCT TTG GTA ATC ACA GTG GCA ACC CTG AGA ACG GCC    3912
Pro Thr Thr Phe Pro Leu Val Ile Thr Val Ala Thr Leu Arg Thr Ala
            1170                1175                1180

AAG ATA ACC AAC GGT TTT AGC ACA GAT CTA GTC ATA GCC ACA GTG TCG    3960
Lys Ile Thr Asn Gly Phe Ser Thr Asp Leu Val Ile Ala Thr Val Ser
        1185                1190                1195

GCA GCT TTG TTA ACT TGG ACC TAT ATC AGC GAC TAC TAC AAA TAC AAG    4008
Ala Ala Leu Leu Thr Trp Thr Tyr Ile Ser Asp Tyr Tyr Lys Tyr Lys
1200                1205                1210                1215

ACT TGG CTA CAG TAC CTC GTC AGC ACG GTG ACT GGA ATC TTC CTG ATA    4056
Thr Trp Leu Gln Tyr Leu Val Ser Thr Val Thr Gly Ile Phe Leu Ile
                    1220                1225                1230

AGG GTG CTG AAG GGA ATA GGC GAA TTG GAT CTG CAC GCC CCA ACC TTG    4104
Arg Val Leu Lys Gly Ile Gly Glu Leu Asp Leu His Ala Pro Thr Leu
                1235                1240                1245

CCG TCT CAC AGA CCC CTC TTT TAC ATC CTT GTA TAC CTT ATT TCC ACT    4152
Pro Ser His Arg Pro Leu Phe Tyr Ile Leu Val Tyr Leu Ile Ser Thr
            1250                1255                1260

GCC GTG GTA ACT AGA TGG AAT CTG GAC GTA GCC GGA TTG TTG CTG CAG    4200
Ala Val Val Thr Arg Trp Asn Leu Asp Val Ala Gly Leu Leu Leu Gln
        1265                1270                1275

TGC GTC CCA ACT CTT TTA ATG GTT TTT ACG ATG TGG GCA GAC ATT CTC    4248
Cys Val Pro Thr Leu Leu Met Val Phe Thr Met Trp Ala Asp Ile Leu
1280                1285                1290                1295

ACC CTA ATT CTC ATA CTA CCT ACT TAT GAG TTA ACA AAG TTA TAC TAC    4296
Thr Leu Ile Leu Ile Leu Pro Thr Tyr Glu Leu Thr Lys Leu Tyr Tyr
                    1300                1305                1310

CTT AAG GAA GTG AAG ATT GGG GCA GAA AGA GGT TGG CTG TGG AAA ACT    4344
Leu Lys Glu Val Lys Ile Gly Ala Glu Arg Gly Trp Leu Trp Lys Thr
                1315                1320                1325

AAC TAT AAG AGG GTA AAC GAC ATC TAC GAG GTC GAC CAA ACT AGC GAA    4392
Asn Tyr Lys Arg Val Asn Asp Ile Tyr Glu Val Asp Gln Thr Ser Glu
            1330                1335                1340

GGG GTT TAC CTT TTC CCT TCT AAA CAG AGG ACG AGC GCT ATA ACT AGT    4440
Gly Val Tyr Leu Phe Pro Ser Lys Gln Arg Thr Ser Ala Ile Thr Ser
        1345                1350                1355

ACC ATG TTG CCA TTA ATC AAA GCC ATA CTC ATT AGC TGC ATC AGC AAC    4488
Thr Met Leu Pro Leu Ile Lys Ala Ile Leu Ile Ser Cys Ile Ser Asn
1360                1365                1370                1375

AAG TGG CAA CTC ATA TAC TTA CTG TAC TTG ATA TTT GAA GTG TCT TAC    4536
Lys Trp Gln Leu Ile Tyr Leu Leu Tyr Leu Ile Phe Glu Val Ser Tyr
                    1380                1385                1390

TAC CTC CAC AAG AAA GTT ATA GAT GAA ATA GCT GGT GGG ACC AAC TTC    4584
Tyr Leu His Lys Lys Val Ile Asp Glu Ile Ala Gly Gly Thr Asn Phe
                1395                1400                1405

GTT TCA AGG CTC GTG GCG GCT TTG ATT GAA GTC AAT TGG GCC TTC GAC    4632
Val Ser Arg Leu Val Ala Ala Leu Ile Glu Val Asn Trp Ala Phe Asp
            1410                1415                1420

AAT GAA GAA GTC AAA GGC TTA AAG AAG TTC TTC TTG CTG TCT AGT AGG    4680
Asn Glu Glu Val Lys Gly Leu Lys Lys Phe Phe Leu Leu Ser Ser Arg
        1425                1430                1435

GTC AAA GAG TTG ATC ATC AAA CAC AAA GTG AGG AAT GAA GTA GTG GTC    4728
```

```
            Val   Lys   Glu   Leu   Ile   Ile   Lys   His   Lys   Val   Arg   Asn   Glu   Val   Val   Val
            1440                    1445                          1450                          1455

CGC   TGG   TTT   GGA   GAT   GAA   GAG   ATT   TAT   GGG   ATG   CCA   AAG   CTG   ATC   GGC            4776
Arg   Trp   Phe   Gly   Asp   Glu   Glu   Ile   Tyr   Gly   Met   Pro   Lys   Leu   Ile   Gly
                        1460                          1465                          1470

TTA   GTT   AAG   GCA   GCA   ACA   CTA   AGT   AGA   AAC   AAA   CAC   TGT   ATG   TTG   TGT            4824
Leu   Val   Lys   Ala   Ala   Thr   Leu   Ser   Arg   Asn   Lys   His   Cys   Met   Leu   Cys
                  1475                          1480                          1485

ACC   GTC   TGT   GAG   GAC   AGA   GAT   TGG   AGA   GGG   GAA   ACT   TGC   CCT   AAA   TGT            4872
Thr   Val   Cys   Glu   Asp   Arg   Asp   Trp   Arg   Gly   Glu   Thr   Cys   Pro   Lys   Cys
                  1490                          1495                          1500

GGG   CGT   TTT   GGA   CCA   CCA   GTG   GTC   TGC   GGT   ATG   ACC   CTA   GCC   GAT   TTC            4920
Gly   Arg   Phe   Gly   Pro   Pro   Val   Val   Cys   Gly   Met   Thr   Leu   Ala   Asp   Phe
                  1505                          1510                          1515

GAA   GAA   AAA   CAC   TAT   AAA   AGG   ATT   TTC   ATT   AGA   GAG   GAC   CAA   TCA   GGC            4968
Glu   Glu   Lys   His   Tyr   Lys   Arg   Ile   Phe   Ile   Arg   Glu   Asp   Gln   Ser   Gly
1520                    1525                          1530                          1535

GGG   CCA   CTT   AGG   GAG   GAG   CAT   GCA   GGG   TAC   TTG   CAG   TAC   AAA   GCC   AGG            5016
Gly   Pro   Leu   Arg   Glu   Glu   His   Ala   Gly   Tyr   Leu   Gln   Tyr   Lys   Ala   Arg
                        1540                          1545                          1550

GGT   CAA   CTG   TTT   TTG   AGG   AAC   CTC   CCA   GTG   TTA   GCT   ACA   AAA   GTC   AAG            5064
Gly   Gln   Leu   Phe   Leu   Arg   Asn   Leu   Pro   Val   Leu   Ala   Thr   Lys   Val   Lys
                  1555                          1560                          1565

ATG   CTC   CTG   GTT   GGT   AAC   CTC   GGG   ACA   GAG   ATT   GGG   GAT   CTG   GAA   CAC            5112
Met   Leu   Leu   Val   Gly   Asn   Leu   Gly   Thr   Glu   Ile   Gly   Asp   Leu   Glu   His
            1570                          1575                          1580

CTT   GGC   TGG   GTG   CTT   AGA   GGG   CCA   GCT   GTT   TGC   AAG   AAG   GTT   ACT   GAA            5160
Leu   Gly   Trp   Val   Leu   Arg   Gly   Pro   Ala   Val   Cys   Lys   Lys   Val   Thr   Glu
            1585                          1590                          1595

CAC   GAA   AGA   TGC   ACC   ACG   TCT   ATA   ATG   GAT   AAG   TTG   ACT   GCT   TTC   TTT            5208
His   Glu   Arg   Cys   Thr   Thr   Ser   Ile   Met   Asp   Lys   Leu   Thr   Ala   Phe   Phe
1600                    1605                          1610                          1615

GGA   GTA   ATG   CCA   AGG   GGC   ACT   ACT   CCC   AGA   GCT   CCC   GTA   AGA   TTC   CCT            5256
Gly   Val   Met   Pro   Arg   Gly   Thr   Thr   Pro   Arg   Ala   Pro   Val   Arg   Phe   Pro
                        1620                          1625                          1630

ACC   TCC   CTC   CTA   AAG   ATA   AGA   AGA   GGG   CTG   GAG   ACT   GGT   TGG   GCT   TAC            5304
Thr   Ser   Leu   Leu   Lys   Ile   Arg   Arg   Gly   Leu   Glu   Thr   Gly   Trp   Ala   Tyr
                  1635                          1640                          1645

ACA   CAC   CAA   GGT   GGC   ATC   AGC   TCA   GTA   GAC   CAT   GTC   ACT   TGT   GGG   AAA            5352
Thr   His   Gln   Gly   Gly   Ile   Ser   Ser   Val   Asp   His   Val   Thr   Cys   Gly   Lys
            1650                          1655                          1660

GAC   TTA   CTG   GTG   TGT   GAC   ACC   ATG   GGT   CGG   ACA   AGG   GTT   GTT   TGC   CAG            5400
Asp   Leu   Leu   Val   Cys   Asp   Thr   Met   Gly   Arg   Thr   Arg   Val   Val   Cys   Gln
                  1665                          1670                          1675

TCA   AAT   AAT   AAG   ATG   ACC   GAC   GAG   TCC   GAA   TAC   GGA   GTC   AAA   ACT   GAC            5448
Ser   Asn   Asn   Lys   Met   Thr   Asp   Glu   Ser   Glu   Tyr   Gly   Val   Lys   Thr   Asp
1680                    1685                          1690                          1695

TCC   GGG   TGC   CCA   GAG   GGA   GCC   AGG   TGT   TAC   GTG   TTT   AAC   CCG   GAA   GCA            5496
Ser   Gly   Cys   Pro   Glu   Gly   Ala   Arg   Cys   Tyr   Val   Phe   Asn   Pro   Glu   Ala
                        1700                          1705                          1710

GTT   AAC   ATA   TCA   GGC   ACT   AAA   GGA   GCC   ATG   GTC   CAC   TTA   CAG   AAA   ACG            5544
Val   Asn   Ile   Ser   Gly   Thr   Lys   Gly   Ala   Met   Val   His   Leu   Gln   Lys   Thr
                  1715                          1720                          1725

GGT   GGA   GAA   TTC   ACC   TGT   GTG   ACA   GCA   TCA   GGA   ACC   CCG   GCC   TTC   TTT            5592
Gly   Gly   Glu   Phe   Thr   Cys   Val   Thr   Ala   Ser   Gly   Thr   Pro   Ala   Phe   Phe
            1730                          1735                          1740

GAC   CTC   AAG   AAC   CTT   AAG   GGC   TGG   TCA   GGG   CTA   CCG   ATA   TTT   GAA   GCA            5640
Asp   Leu   Lys   Asn   Leu   Lys   Gly   Trp   Ser   Gly   Leu   Pro   Ile   Phe   Glu   Ala
                  1745                          1750                          1755

TCA   AGT   GGA   AGG   GTA   GTC   GGA   AGG   GTC   AAG   GTC   GGG   AAG   AAC   GAG   GAT            5688
```

```
Ser  Ser  Gly  Arg  Val  Val  Gly  Arg  Val  Lys  Val  Gly  Lys  Asn  Glu  Asp
1760                 1765                     1770                     1775

TCC  AAA  CCA  ACC  AAG  CTC  ATG  AGT  GGG  ATA  CAA  ACG  GTT  TCT  AAA  AGC        5736
Ser  Lys  Pro  Thr  Lys  Leu  Met  Ser  Gly  Ile  Gln  Thr  Val  Ser  Lys  Ser
                    1780                     1785                     1790

GCC  ACA  GAC  TTG  ACG  GAG  ATG  GTG  AAG  AAG  ATA  ACG  ACC  ATG  AAC  AGG        5784
Ala  Thr  Asp  Leu  Thr  Glu  Met  Val  Lys  Lys  Ile  Thr  Thr  Met  Asn  Arg
          1795                     1800                     1805

GGA  GAG  TTC  AGA  CAA  ATA  ACC  CTG  GCC  ACA  GGT  GCC  GGA  AAA  ACT  ACA        5832
Gly  Glu  Phe  Arg  Gln  Ile  Thr  Leu  Ala  Thr  Gly  Ala  Gly  Lys  Thr  Thr
               1810                     1815                     1820

GAG  CTC  CCT  AGA  TCA  GTT  ATA  GAA  GAG  ATA  GGG  AGG  CAT  AAG  AGG  GTG        5880
Glu  Leu  Pro  Arg  Ser  Val  Ile  Glu  Glu  Ile  Gly  Arg  His  Lys  Arg  Val
                    1825                     1830                     1835

TTG  GTC  TTA  ATC  CCC  TTG  AGG  GCG  GCA  GCA  GAA  TCA  GTA  TAC  CAA  TAC        5928
Leu  Val  Leu  Ile  Pro  Leu  Arg  Ala  Ala  Ala  Glu  Ser  Val  Tyr  Gln  Tyr
1840                     1845                     1850                     1855

ATG  AGA  CAG  AAA  CAT  CCG  AGT  ATA  GCA  TTC  AAT  CTA  AGG  ATA  GGT  GAG        5976
Met  Arg  Gln  Lys  His  Pro  Ser  Ile  Ala  Phe  Asn  Leu  Arg  Ile  Gly  Glu
          1860                     1865                     1870

ATG  AAG  GAA  GGT  GAT  ATG  GCC  ACG  GGA  ATA  ACC  TAT  GCC  TCT  TAC  GGT        6024
Met  Lys  Glu  Gly  Asp  Met  Ala  Thr  Gly  Ile  Thr  Tyr  Ala  Ser  Tyr  Gly
               1875                     1880                     1885

TAC  TTT  TGC  CAG  ATG  TCA  CAA  CCC  AAG  CTG  AGA  GCC  GCA  ATG  GTA  GAA        6072
Tyr  Phe  Cys  Gln  Met  Ser  Gln  Pro  Lys  Leu  Arg  Ala  Ala  Met  Val  Glu
                    1890                     1895                     1900

TAT  TCC  TTT  ATA  TTC  CTA  GAT  GAG  TAT  CAT  TGT  GCT  ACC  CCA  GAA  CAA        6120
Tyr  Ser  Phe  Ile  Phe  Leu  Asp  Glu  Tyr  His  Cys  Ala  Thr  Pro  Glu  Gln
1905                     1910                     1915

CTG  GCA  ATC  ATG  GGG  AAG  ATC  CAC  AGA  TTC  TCA  GAA  AAC  CTG  CGG  GTG        6168
Leu  Ala  Ile  Met  Gly  Lys  Ile  His  Arg  Phe  Ser  Glu  Asn  Leu  Arg  Val
1920                     1925                     1930                     1935

GTA  GCT  ATG  ACA  GCG  ACA  CCG  GCA  GGC  ACA  GTA  ACA  ACC  ACT  GGG  CAG        6216
Val  Ala  Met  Thr  Ala  Thr  Pro  Ala  Gly  Thr  Val  Thr  Thr  Thr  Gly  Gln
               1940                     1945                     1950

AAA  CAC  CCT  ATA  GAG  GAA  TTT  ATA  GCC  CCG  GAA  GTG  ATG  AAA  GGA  GAA        6264
Lys  His  Pro  Ile  Glu  Glu  Phe  Ile  Ala  Pro  Glu  Val  Met  Lys  Gly  Glu
          1955                     1960                     1965

GAC  TTG  GGT  TCT  GAG  TAC  TTA  GAT  ATT  GCC  GGA  CTG  AAG  ATA  CCA  GTA        6312
Asp  Leu  Gly  Ser  Glu  Tyr  Leu  Asp  Ile  Ala  Gly  Leu  Lys  Ile  Pro  Val
               1970                     1975                     1980

GAG  GAG  ATG  AAG  AAT  AAC  ATG  CTA  GTT  TTT  GTG  CCC  ACC  AGG  AAC  ATG        6360
Glu  Glu  Met  Lys  Asn  Asn  Met  Leu  Val  Phe  Val  Pro  Thr  Arg  Asn  Met
1985                     1990                     1995

GCG  GTA  GAG  GCG  GCA  AAG  AAA  TTG  AAG  GCC  AAA  GGA  TAC  AAC  TCG  GGC        6408
Ala  Val  Glu  Ala  Ala  Lys  Lys  Leu  Lys  Ala  Lys  Gly  Tyr  Asn  Ser  Gly
2000                     2005                     2010                     2015

TAC  TAC  TAC  AGC  GGA  GAG  GAC  CCA  TCT  AAC  CTG  AGG  GTG  GTG  ACG  TCG        6456
Tyr  Tyr  Tyr  Ser  Gly  Glu  Asp  Pro  Ser  Asn  Leu  Arg  Val  Val  Thr  Ser
               2020                     2025                     2030

CAG  TCC  CCA  TAC  GTG  GTG  GTA  GCA  ACC  AAC  GCA  ATA  GAA  TCG  GGC  GTT        6504
Gln  Ser  Pro  Tyr  Val  Val  Val  Ala  Thr  Asn  Ala  Ile  Glu  Ser  Gly  Val
               2035                     2040                     2045

ACC  CTC  CCG  GAC  CTG  GAC  GTG  GTT  GTC  GAC  ACG  GGA  CTC  AAG  TGT  GAA        6552
Thr  Leu  Pro  Asp  Leu  Asp  Val  Val  Val  Asp  Thr  Gly  Leu  Lys  Cys  Glu
               2050                     2055                     2060

AAA  AGA  ATC  CGA  CTG  TCA  CCC  AAG  ATG  CCT  TTC  ATA  GTG  ACG  GGC  CTG        6600
Lys  Arg  Ile  Arg  Leu  Ser  Pro  Lys  Met  Pro  Phe  Ile  Val  Thr  Gly  Leu
2065                     2070                     2075

AAA  AGA  ATG  GCC  GTC  ACT  ATT  GGG  GAA  CAA  GCC  CAG  AGA  AGA  GGG  AGG        6648
```

```
Lys Arg Met Ala Val Thr Ile Gly Glu Gln Ala Gln Arg Arg Gly Arg
2080                2085                2090                2095

GTT GGA AGA GTG AAG CCC GGG AGA TAC TAC AGG AGT CAA GAA ACA CCT    6696
Val Gly Arg Val Lys Pro Gly Arg Tyr Tyr Arg Ser Gln Glu Thr Pro
            2100                2105                2110

GTC GGC TCT AAA GAC TAC CAT TAT GAC TTA TTG CAA GCC CAG AGG TAC    6744
Val Gly Ser Lys Asp Tyr His Tyr Asp Leu Leu Gln Ala Gln Arg Tyr
            2115                2120                2125

GGC ATA GAA GAT GGG ATA AAT ATC ACC AAA TCC TTC AGA GAG ATG AAC    6792
Gly Ile Glu Asp Gly Ile Asn Ile Thr Lys Ser Phe Arg Glu Met Asn
            2130                2135                2140

TAC GAC TGG AGC CTT TAT GAG GAA GAT AGC CTG ATG ATC ACA CAA CTG    6840
Tyr Asp Trp Ser Leu Tyr Glu Glu Asp Ser Leu Met Ile Thr Gln Leu
            2145                2150                2155

GAA ATC CTC AAC AAC CTG TTG ATA TCA GAA GAG CTG CCG ATG GCA GTA    6888
Glu Ile Leu Asn Asn Leu Leu Ile Ser Glu Glu Leu Pro Met Ala Val
2160                2165                2170                2175

AAA AAT ATA ATG GCC AGG ACC GAC CAC CCA GAA CCA ATT CAA CTC GCG    6936
Lys Asn Ile Met Ala Arg Thr Asp His Pro Glu Pro Ile Gln Leu Ala
            2180                2185                2190

TAT AAC AGC TAC GAG ACA CAG GTG CCG GTA TTA TTC CCA AAA ATA AGA    6984
Tyr Asn Ser Tyr Glu Thr Gln Val Pro Val Leu Phe Pro Lys Ile Arg
            2195                2200                2205

AAT GGA GAG GTG ACT GAT ACT TAC GAT AAT TAC ACC TTC CTC AAT GCA    7032
Asn Gly Glu Val Thr Asp Thr Tyr Asp Asn Tyr Thr Phe Leu Asn Ala
            2210                2215                2220

AGA AAA TTG GGA GAT GAC GTA CCC CCC TAC GTG TAT GCT ACA GAG GAT    7080
Arg Lys Leu Gly Asp Asp Val Pro Pro Tyr Val Tyr Ala Thr Glu Asp
            2225                2230                2235

GAG GAC TTG GCA GTG GAA CTG TTG GGC CTA GAT TGG CCG GAC CCA GGA    7128
Glu Asp Leu Ala Val Glu Leu Leu Gly Leu Asp Trp Pro Asp Pro Gly
2240                2245                2250                2255

AAC CAA GGC ACC GTG GAA GCT GGC AGA GCA CTA AAA CAG GTG GTT GGT    7176
Asn Gln Gly Thr Val Glu Ala Gly Arg Ala Leu Lys Gln Val Val Gly
            2260                2265                2270

CTA TCA ACA GCA GAG AAC GCC CTG CTA GTC GCC CTG TTC GGC TAC GTG    7224
Leu Ser Thr Ala Glu Asn Ala Leu Leu Val Ala Leu Phe Gly Tyr Val
            2275                2280                2285

GGG TAC CAG GCG CTT TCA AAG AGA CAT ATA CCA GTG GTC ACA GAT ATA    7272
Gly Tyr Gln Ala Leu Ser Lys Arg His Ile Pro Val Val Thr Asp Ile
            2290                2295                2300

TAT TCA GTA GAA GAT CAC AGG CTA GAG GAC ACT ACG CAC CTA CAG TAT    7320
Tyr Ser Val Glu Asp His Arg Leu Glu Asp Thr Thr His Leu Gln Tyr
            2305                2310                2315

GCT CCG AAT GCC ATC AAG ACG GAG GGG AAG GAA ACT GAA TTG AAG GAG    7368
Ala Pro Asn Ala Ile Lys Thr Glu Gly Lys Glu Thr Glu Leu Lys Glu
2320                2325                2330                2335

CTG GCT CAG GGG GAT GTG CAG AGA TGT GTG GAA GCA GTG ACC AAT TAT    7416
Leu Ala Gln Gly Asp Val Gln Arg Cys Val Glu Ala Val Thr Asn Tyr
            2340                2345                2350

GCG AGA GAG GGC ATC CAA TTC ATG AAG TCG CAG GCA CTG AAA GTG AGA    7464
Ala Arg Glu Gly Ile Gln Phe Met Lys Ser Gln Ala Leu Lys Val Arg
            2355                2360                2365

GAA ACC CCT ACC TAT AAA GAG ACA ATG AAC ACC GTG GCA GAT TAT GTG    7512
Glu Thr Pro Thr Tyr Lys Glu Thr Met Asn Thr Val Ala Asp Tyr Val
            2370                2375                2380

AAA AAG TTT ATT GAG GCA CTG ACG GAT AGC AAG GAA GAC ATC ATT AAA    7560
Lys Lys Phe Ile Glu Ala Leu Thr Asp Ser Lys Glu Asp Ile Ile Lys
            2385                2390                2395

TAT GGG CTG TGG GGG GCA CAT ACG GCA TTG TAT AAG AGC ATT GGT GCC    7608
```

```
                Tyr Gly Leu Trp Gly Ala His Thr Ala Leu Tyr Lys Ser Ile Gly Ala
                2400            2405                2410                2415

AGG CTT GGT CAC GAA ACC GCG TTC GCA ACT CTA GTT GTG AAG TGG TTG        7656
Arg Leu Gly His Glu Thr Ala Phe Ala Thr Leu Val Val Lys Trp Leu
                2420                2425                2430

GCA TTT GGG GGG GAG TCA ATA TCA GAC CAC ATA AAG CAA GCG GCC ACA        7704
Ala Phe Gly Gly Glu Ser Ile Ser Asp His Ile Lys Gln Ala Ala Thr
                    2435                2440                2445

GAC TTG GTC GTT TAT TAC ATT ATT AAC AGA CCT CAA TTC CCA GGA GAC        7752
Asp Leu Val Val Tyr Tyr Ile Ile Asn Arg Pro Gln Phe Pro Gly Asp
                2450                2455                2460

ACA GAA ACA CAA CAA GAA GGG AGA AAA TTT GTT GCC AGC CTG CTA GTC        7800
Thr Glu Thr Gln Gln Glu Gly Arg Lys Phe Val Ala Ser Leu Leu Val
                2465                2470                2475

TCA GCT CTA GCG ACT TAT ACA TAC AAG AGC TGG AAC TAC AAT AAT CTG        7848
Ser Ala Leu Ala Thr Tyr Thr Tyr Lys Ser Trp Asn Tyr Asn Asn Leu
2480                2485                2490                2495

TCC AAA ATA GTT GAA CCG GCT TTG GCT ACC CTG CCC TAT GCC GCT AAA        7896
Ser Lys Ile Val Glu Pro Ala Leu Ala Thr Leu Pro Tyr Ala Ala Lys
                    2500                2505                2510

GCC CTC AAG CTA TTT GCT CCT ACC CGA CTG GAG AGC GTT GTC ATA CTG        7944
Ala Leu Lys Leu Phe Ala Pro Thr Arg Leu Glu Ser Val Val Ile Leu
                2515                2520                2525

AGC ACT GCA ATC TAC AAA ACA TAC CTA TCA ATA AGG CGA GGC AAA AGT        7992
Ser Thr Ala Ile Tyr Lys Thr Tyr Leu Ser Ile Arg Arg Gly Lys Ser
                2530                2535                2540

GAT GGT CTG CTA GGT ACA GGG GTT AGC GCG GCC ATG GAA ATT ATG TCA        8040
Asp Gly Leu Leu Gly Thr Gly Val Ser Ala Ala Met Glu Ile Met Ser
                2545                2550                2555

CAA AAC CCA GTA TCT GTG GGT ATA GCA GTT ATG CTA GGG GTA GGG GCT        8088
Gln Asn Pro Val Ser Val Gly Ile Ala Val Met Leu Gly Val Gly Ala
2560                2565                2570                2575

GTA GCA GCC CAC AAT GCA ATT GAA GCC AGT GAG CAA AAA AGA ACA CTA        8136
Val Ala Ala His Asn Ala Ile Glu Ala Ser Glu Gln Lys Arg Thr Leu
                    2580                2585                2590

CTT ATG AAA GTC TTT GTG AAA AAC TTC TTA GAC CAG GCC GCC ACC GAC        8184
Leu Met Lys Val Phe Val Lys Asn Phe Leu Asp Gln Ala Ala Thr Asp
                2595                2600                2605

GAA CTA GTC AAA GAG AGC CCT GAG AAA ATA ATA ATG GCT TTG TTC GAA        8232
Glu Leu Val Lys Glu Ser Pro Glu Lys Ile Ile Met Ala Leu Phe Glu
                2610                2615                2620

GCG GTG CAA ACG GTG GGC AAC CCT CTT AGA TTA GTG TAC CAC CTC TAT        8280
Ala Val Gln Thr Val Gly Asn Pro Leu Arg Leu Val Tyr His Leu Tyr
                2625                2630                2635

GGA GTT TTC TAT AAA GGG TGG GAA GCA AAA GAG TTG GCC CAA AGA ACA        8328
Gly Val Phe Tyr Lys Gly Trp Glu Ala Lys Glu Leu Ala Gln Arg Thr
2640                2645                2650                2655

GCC GGC AGG AAC CTT TTC ACC TTG ATA ATG TTC GAG GCT GTG GAA CTA        8376
Ala Gly Arg Asn Leu Phe Thr Leu Ile Met Phe Glu Ala Val Glu Leu
                    2660                2665                2670

CTG GGA GTA GAC AGT GAG GGA AAA ATT CGC CAG CTA TCG AGC AAT TAC        8424
Leu Gly Val Asp Ser Glu Gly Lys Ile Arg Gln Leu Ser Ser Asn Tyr
                2675                2680                2685

ATA CTA GAG CTC TTG TAT AAG TTC CGC GAC AAT ATC AAG TCT AGT GTG        8472
Ile Leu Glu Leu Leu Tyr Lys Phe Arg Asp Asn Ile Lys Ser Ser Val
                2690                2695                2700

AGG GAG ATA GCA ATC AGC TGG GCC CCC GCC CCC TTT AGT TGC GAT TGG        8520
Arg Glu Ile Ala Ile Ser Trp Ala Pro Ala Pro Phe Ser Cys Asp Trp
                2705                2710                2715

ACA CCA ACA GAT GAC AGA ATA GGG CTT CCC CAT GAC AAT TAC CTC CGA        8568
```

```
Thr  Pro  Thr  Asp  Asp  Arg  Ile  Gly  Leu  Pro  His  Asp  Asn  Tyr  Leu  Arg
2720                2725                     2730                     2735

GTG  GAG  ACA  AAG  TGC  CCC  TGT  GGT  TAC  AGG  ATG  AAA  GCG  GTA  AAA  AAC      8616
Val  Glu  Thr  Lys  Cys  Pro  Cys  Gly  Tyr  Arg  Met  Lys  Ala  Val  Lys  Asn
          2740                     2745                     2750

TGC  GCT  GGG  GAG  TTG  AGA  CTT  CTG  GAG  GAA  GGG  GGT  TCA  TTC  CTC  TGC      8664
Cys  Ala  Gly  Glu  Leu  Arg  Leu  Leu  Glu  Glu  Gly  Gly  Ser  Phe  Leu  Cys
               2755                     2760                     2765

AGA  AAT  AAA  TTC  GGT  AGA  GGC  TCA  CAA  AAC  TAC  AGG  GTG  ACA  AAA  TAC      8712
Arg  Asn  Lys  Phe  Gly  Arg  Gly  Ser  Gln  Asn  Tyr  Arg  Val  Thr  Lys  Tyr
          2770                     2775                     2780

TAT  GAT  GAC  AAT  TTA  TCA  GAA  ATA  AAA  CCA  GTG  ATA  AGA  ATG  GAA  GGA      8760
Tyr  Asp  Asp  Asn  Leu  Ser  Glu  Ile  Lys  Pro  Val  Ile  Arg  Met  Glu  Gly
     2785                     2790                     2795

CAC  GTG  GAA  CTG  TAT  TAC  AAG  GGG  GCC  ACT  ATC  AAA  CTG  GAT  TTT  AAC      8808
His  Val  Glu  Leu  Tyr  Tyr  Lys  Gly  Ala  Thr  Ile  Lys  Leu  Asp  Phe  Asn
2800                2805                     2810                     2815

AAC  AGT  AAA  ACG  GTA  CTG  GCA  ACT  GAC  AAA  TGG  GAG  GTT  GAC  CAC  TCC      8856
Asn  Ser  Lys  Thr  Val  Leu  Ala  Thr  Asp  Lys  Trp  Glu  Val  Asp  His  Ser
               2820                     2825                     2830

ACC  CTG  GTT  AGG  GCA  CTC  AAG  AGG  TAC  ACA  GGG  GCT  GGA  TAT  CGA  GGG      8904
Thr  Leu  Val  Arg  Ala  Leu  Lys  Arg  Tyr  Thr  Gly  Ala  Gly  Tyr  Arg  Gly
          2835                     2840                     2845

GCG  TAT  TTG  GGT  GAG  AAA  CCT  AAC  CAT  AAA  CAT  CTG  ATA  CAG  AGA  GAC      8952
Ala  Tyr  Leu  Gly  Glu  Lys  Pro  Asn  His  Lys  His  Leu  Ile  Gln  Arg  Asp
     2850                     2855                     2860

TGT  GCA  ACG  ATT  ACC  AAA  GAC  AAG  GTC  TGC  TTC  ATC  AAA  ATG  AAG  AGA      9000
Cys  Ala  Thr  Ile  Thr  Lys  Asp  Lys  Val  Cys  Phe  Ile  Lys  Met  Lys  Arg
2865                2870                     2875

GGG  TGT  GCG  TTC  ACT  TAT  GAC  CTA  TCC  CTC  CAC  AAC  CTT  ACC  CGG  CTA      9048
Gly  Cys  Ala  Phe  Thr  Tyr  Asp  Leu  Ser  Leu  His  Asn  Leu  Thr  Arg  Leu
2880                     2885                     2890                     2895

ATC  GAA  TTG  GTA  CAC  AAG  AAT  AAC  CTG  GAA  GAT  AGA  GAA  ATC  CCT  GCT      9096
Ile  Glu  Leu  Val  His  Lys  Asn  Asn  Leu  Glu  Asp  Arg  Glu  Ile  Pro  Ala
               2900                     2905                     2910

GTG  ACG  GTT  ACA  ACC  TGG  CTG  GCC  TAC  ACA  TTT  GTG  AAT  GAA  GAC  ATA      9144
Val  Thr  Val  Thr  Thr  Trp  Leu  Ala  Tyr  Thr  Phe  Val  Asn  Glu  Asp  Ile
          2915                     2920                     2925

GGG  ACC  ATA  AAA  CCA  ACT  TTT  GGG  GAA  AAG  GTG  ACA  CCG  GAG  AAA  CAG      9192
Gly  Thr  Ile  Lys  Pro  Thr  Phe  Gly  Glu  Lys  Val  Thr  Pro  Glu  Lys  Gln
     2930                     2935                     2940

GAG  GAG  GTA  GTC  TTG  CAG  CCT  GCT  GTG  GTG  GTG  GAC  ACA  ACA  GAT  GTA      9240
Glu  Glu  Val  Val  Leu  Gln  Pro  Ala  Val  Val  Val  Asp  Thr  Thr  Asp  Val
2945                     2950                     2955

GCC  GTG  ACC  GTG  GTA  GGG  GAA  ACC  TCT  ACT  ATG  ACT  ACA  GGG  GAG  ACC      9288
Ala  Val  Thr  Val  Val  Gly  Glu  Thr  Ser  Thr  Met  Thr  Thr  Gly  Glu  Thr
2960                     2965                     2970                     2975

CCG  ACA  ACA  TTT  ACC  AGC  TTA  GGT  TCG  GAC  TCG  AAG  GTC  CGA  CAA  GTC      9336
Pro  Thr  Thr  Phe  Thr  Ser  Leu  Gly  Ser  Asp  Ser  Lys  Val  Arg  Gln  Val
               2980                     2985                     2990

CTG  AAG  CTG  GGC  GTG  GAC  GAT  GGT  CAA  TAC  CCC  GGG  CCT  AAT  CAG  CAG      9384
Leu  Lys  Leu  Gly  Val  Asp  Asp  Gly  Gln  Tyr  Pro  Gly  Pro  Asn  Gln  Gln
          2995                     3000                     3005

AGA  GCA  AGC  CTG  CTC  GAA  GCT  ATA  CAA  GGT  GTG  GAT  GAA  AGG  CCC  TCG      9432
Arg  Ala  Ser  Leu  Leu  Glu  Ala  Ile  Gln  Gly  Val  Asp  Glu  Arg  Pro  Ser
     3010                     3015                     3020

GTA  CTG  ATA  CTG  GGG  TCT  GAT  AAG  GCC  ACC  TCC  AAT  AGG  GTC  AAG  ACC      9480
Val  Leu  Ile  Leu  Gly  Ser  Asp  Lys  Ala  Thr  Ser  Asn  Arg  Val  Lys  Thr
3025                     3030                     3035

GCA  AAG  AAT  GTG  AAG  ATA  TAT  AGG  AGC  AGG  GAC  CCC  CTG  GAA  CTG  AGA      9528
```

```
Ala Lys Asn Val Lys Ile Tyr Arg Ser Arg Asp Pro Leu Glu Leu Arg
3040                3045                3050                3055

GAA ATG ATG AAA AGG GGA AAA ATC CTA GTC GTA GCC TTG TCT AGA GTC     9576
Glu Met Met Lys Arg Gly Lys Ile Leu Val Val Ala Leu Ser Arg Val
            3060                3065                3070

GAT ACC GCT CTG CTG AAA TTC GTT GAT TAC AAA GGC ACC TTC CTG ACC     9624
Asp Thr Ala Leu Leu Lys Phe Val Asp Tyr Lys Gly Thr Phe Leu Thr
                3075                3080                3085

AGA GAG ACC CTA GAG GCA TTA AGT CTG GGT AAG CCT AAG AAA AGA GAC     9672
Arg Glu Thr Leu Glu Ala Leu Ser Leu Gly Lys Pro Lys Lys Arg Asp
                    3090                3095                3100

ATA ACT AAA GCA GAA GCA CAA TGG CTG CTG CGC CTC GAA GAC CAA ATA     9720
Ile Thr Lys Ala Glu Ala Gln Trp Leu Leu Arg Leu Glu Asp Gln Ile
        3105                3110                3115

GAA GAG CTG CCT GAC TGG TTC GCA GCC AAG GAA CCC ATA TTT CTA GAA     9768
Glu Glu Leu Pro Asp Trp Phe Ala Ala Lys Glu Pro Ile Phe Leu Glu
3120                3125                3130                3135

GCC AAC ATT AAA CGT GAC AAG TAT CAC CTG GTA GGG GAC ATA GCC ACT     9816
Ala Asn Ile Lys Arg Asp Lys Tyr His Leu Val Gly Asp Ile Ala Thr
            3140                3145                3150

ATT AAA GAA AAA GCC AAA CAA CTG GGG GCA ACA GAC TCC ACA AAG ATA     9864
Ile Lys Glu Lys Ala Lys Gln Leu Gly Ala Thr Asp Ser Thr Lys Ile
                3155                3160                3165

TCA AAG GAG GTT GGC GCG AAA GTG TAT TCT ATG AAG CTG AGT AAC TGG     9912
Ser Lys Glu Val Gly Ala Lys Val Tyr Ser Met Lys Leu Ser Asn Trp
                    3170                3175                3180

GTG ATA CAA GAA GAG AAT AAA CAA GGC AGC CTT GCC CCC CTG TTT GAA     9960
Val Ile Gln Glu Glu Asn Lys Gln Gly Ser Leu Ala Pro Leu Phe Glu
        3185                3190                3195

GAG CTC CTG CAA CAG TGC CCA CCC GGG GGC CAG AAC AAA ACC ACA CAT    10008
Glu Leu Leu Gln Gln Cys Pro Pro Gly Gly Gln Asn Lys Thr Thr His
3200                3205                3210                3215

ATG GTC TCA GCC TAC CAA CTA GCT CAA GGG AAT TGG GTG CCA GTT AGT    10056
Met Val Ser Ala Tyr Gln Leu Ala Gln Gly Asn Trp Val Pro Val Ser
            3220                3225                3230

TGC CAC GTG TTC ATG GGG ACC ATA CCC GCC AGA AGA ACC AAG ACT CAT    10104
Cys His Val Phe Met Gly Thr Ile Pro Ala Arg Arg Thr Lys Thr His
                3235                3240                3245

CCT TAT GAG GCA TAC GTT AAG CTA AGG GAG TTG GTA GAT GAA CAT AAG    10152
Pro Tyr Glu Ala Tyr Val Lys Leu Arg Glu Leu Val Asp Glu His Lys
                    3250                3255                3260

ATG AAG GCA TTA TGT GGC GGA TCA GGC CTA AGT AAG CAC AAC GAA TGG    10200
Met Lys Ala Leu Cys Gly Gly Ser Gly Leu Ser Lys His Asn Glu Trp
        3265                3270                3275

GTA ATT GGC AAG GTC AAG TAT CAA GGA AAC CTG AGG ACC AAA CAC ATG    10248
Val Ile Gly Lys Val Lys Tyr Gln Gly Asn Leu Arg Thr Lys His Met
3280                3285                3290                3295

TTG AAC CCC GGA AAG GTG GCG GAG CAA CTG CAC AGA GAA GGG TAC AGG    10296
Leu Asn Pro Gly Lys Val Ala Glu Gln Leu His Arg Glu Gly Tyr Arg
            3300                3305                3310

CAC AAT GTG TAT AAT AAG ACA ATA GGT TCA GTG ATG ACA GCA ACT GGT    10344
His Asn Val Tyr Asn Lys Thr Ile Gly Ser Val Met Thr Ala Thr Gly
                3315                3320                3325

ATC AGG CTG GAG AAG TTA CCT GTG GTT AGG GCC CAA ACA GAC ACA ACC    10392
Ile Arg Leu Glu Lys Leu Pro Val Val Arg Ala Gln Thr Asp Thr Thr
                    3330                3335                3340

AAC TTC CAC CAA GCA ATA AGG GAT AAA ATA GAC AAG GAG GAG AAC CTA    10440
Asn Phe His Gln Ala Ile Arg Asp Lys Ile Asp Lys Glu Glu Asn Leu
        3345                3350                3355

CAG ACC CCT GGC TTG CAT AAG AAG TTA ATG GAA GTC TTC AAT GCA TTA    10488
```

```
Gln Thr Pro Gly Leu His Lys Lys Leu Met Glu Val Phe Asn Ala Leu
3360                3365                3370                3375

AAA AGA CCC GAG CTT GAG GCC TCT TAT GAC GCT GTG GAT TGG GAG GAA    10536
Lys Arg Pro Glu Leu Glu Ala Ser Tyr Asp Ala Val Asp Trp Glu Glu
        3380                3385                3390

TTG GAG AGA GGA ATA AAT AGG AAG GGT GCT GCT GGT TTC TTC GAA CGC    10584
Leu Glu Arg Gly Ile Asn Arg Lys Gly Ala Ala Gly Phe Phe Glu Arg
            3395                3400                3405

AAG AAC ATA GGA GAG GTT TTG GAT TCG GAA AAA AAT AAA GTC GAA GAG    10632
Lys Asn Ile Gly Glu Val Leu Asp Ser Glu Lys Asn Lys Val Glu Glu
                3410                3415                3420

GTT ATT GAC AGT TTG AAA AAA GGT AGG AAT ATC AGA TAC TAC GAA ACT    10680
Val Ile Asp Ser Leu Lys Lys Gly Arg Asn Ile Arg Tyr Tyr Glu Thr
3425                3430                3435

GCA ATC CCG AAA AAC GAG AAG AGG GAT GTC AAT GAT GAC TGG ACC GCT    10728
Ala Ile Pro Lys Asn Glu Lys Arg Asp Val Asn Asp Asp Trp Thr Ala
        3440                3445                3450                3455

GGT GAC TTC GTA GAT GAG AAG AAG CCA AGA GTG ATA CAA TAC CCT GAG    10776
Gly Asp Phe Val Asp Glu Lys Lys Pro Arg Val Ile Gln Tyr Pro Glu
            3460                3465                3470

GCT AAA ACT AGG TTG GCT ATT ACT AAG GTA ATG TAC AAG TGG GTC AAA    10824
Ala Lys Thr Arg Leu Ala Ile Thr Lys Val Met Tyr Lys Trp Val Lys
                3475                3480                3485

CAG AAG CCA GTT GTC ATA CCG GGT TAT GAA GGT AAG ACA CCC CTG TTT    10872
Gln Lys Pro Val Val Ile Pro Gly Tyr Glu Gly Lys Thr Pro Leu Phe
        3490                3495                3500

CAA ATT TTT GAC AAA GTG AAG AAA GAA TGG GAT CAA TTC CAA AAC CCT    10920
Gln Ile Phe Asp Lys Val Lys Lys Glu Trp Asp Gln Phe Gln Asn Pro
        3505                3510                3515

GTG GCA GTT AGC TTT GAT ACC AAA GCG TGG GAT ACC CAG GTA ACC ACA    10968
Val Ala Val Ser Phe Asp Thr Lys Ala Trp Asp Thr Gln Val Thr Thr
3520                3525                3530                3535

AGG GAT TTG GAG CTA ATA AGG GAT ATA CAG AAG TTC TAT TTT AAA AAG    11016
Arg Asp Leu Glu Leu Ile Arg Asp Ile Gln Lys Phe Tyr Phe Lys Lys
            3540                3545                3550

AAA TGG CAC AAA TTC ATT GAC ACC CTA ACC AAG CAC ATG TCA GAA GTA    11064
Lys Trp His Lys Phe Ile Asp Thr Leu Thr Lys His Met Ser Glu Val
        3555                3560                3565

CCC GTA ATC AGT GCC GAC GGG GAG GTA TAC ATA AGG AAA GGT CAG AGA    11112
Pro Val Ile Ser Ala Asp Gly Glu Val Tyr Ile Arg Lys Gly Gln Arg
        3570                3575                3580

GGC AGT GGG CAA CCT GAC ACG AGC GCA GGC AAC AGC ATG TTG AAT GTG    11160
Gly Ser Gly Gln Pro Asp Thr Ser Ala Gly Asn Ser Met Leu Asn Val
        3585                3590                3595

TTG ACA ATG GTG TAT GCC TTC TGC GAG GCC ACG GGG GTA CCC TAC AAG    11208
Leu Thr Met Val Tyr Ala Phe Cys Glu Ala Thr Gly Val Pro Tyr Lys
3600                3605                3610                3615

AGT TTT GAC AGA GTG GCA AAG ATC CAT GTC TGC GGG GAT GAT GGT TTC    11256
Ser Phe Asp Arg Val Ala Lys Ile His Val Cys Gly Asp Asp Gly Phe
            3620                3625                3630

CTG ATT ACC GAA AGA GCT CTC GGT GAG AAA TTT GCG AGT AAA GGA GTC    11304
Leu Ile Thr Glu Arg Ala Leu Gly Glu Lys Phe Ala Ser Lys Gly Val
            3635                3640                3645

CAG ATC CTA TAC GAA GCT GGG AAG CCT CAA AAG ATC ACT GAA GGG GAC    11352
Gln Ile Leu Tyr Glu Ala Gly Lys Pro Gln Lys Ile Thr Glu Gly Asp
        3650                3655                3660

AAG ATG AAA GTA GCC TAT CAG TTT GAT GAT ATC GAG TTC TGC TCC CAT    11400
Lys Met Lys Val Ala Tyr Gln Phe Asp Asp Ile Glu Phe Cys Ser His
    3665                3670                3675

ACA CCA GTA CAA GTG AGG TGG TCA GAC AAT ACT TCC AGC TAC ATG CCG    11448
```

-continued

| | | | | | | | | | | | | | | | |
|---|---|---|---|---|---|---|---|---|---|---|---|---|---|---|---|
| Thr | Pro | Val | Gln | Val | Arg | Trp | Ser | Asp | Asn | Thr | Ser | Ser | Tyr | Met | Pro |
| 3680 | | | | | 3685 | | | | 3690 | | | | | | 3695 |

```
GGA  AGG  AAC  ACG  ACT  ACA  ATC  CTG  GCT  AAA  ATG  GCT  ACA  AGG  TTG  GAT      11496
Gly  Arg  Asn  Thr  Thr  Thr  Ile  Leu  Ala  Lys  Met  Ala  Thr  Arg  Leu  Asp
                         3700                    3705                    3710

TCC  AGT  GGT  GAG  AGG  GGT  ACT  ATA  GCA  TAT  GAG  AAG  GCA  GTG  GCG  TTC      11544
Ser  Ser  Gly  Glu  Arg  Gly  Thr  Ile  Ala  Tyr  Glu  Lys  Ala  Val  Ala  Phe
                    3715                    3720                    3725

AGC  TTT  TTG  TTG  ATG  TAC  TCC  TGG  AAC  CCA  CTG  ATC  AGA  AGG  ATA  TGC      11592
Ser  Phe  Leu  Leu  Met  Tyr  Ser  Trp  Asn  Pro  Leu  Ile  Arg  Arg  Ile  Cys
                         3730                    3735                    3740

TTA  CTG  GTG  TTG  TCA  ACT  GAG  TTG  CAA  GTG  AGA  CCA  GGG  AAG  TCA  ACC      11640
Leu  Leu  Val  Leu  Ser  Thr  Glu  Leu  Gln  Val  Arg  Pro  Gly  Lys  Ser  Thr
                    3745                    3750                    3755

ACC  TAT  TAC  TAT  GAA  GGG  GAC  CCA  ATA  TCC  GCT  TAC  AAG  GAA  GTC  ATT      11688
Thr  Tyr  Tyr  Tyr  Glu  Gly  Asp  Pro  Ile  Ser  Ala  Tyr  Lys  Glu  Val  Ile
3760                    3765                    3770                    3775

GGC  CAC  AAT  CTC  TTT  GAC  CTT  AAA  AGA  ACA  AGC  TTC  GAA  AAG  CTA  GCA      11736
Gly  His  Asn  Leu  Phe  Asp  Leu  Lys  Arg  Thr  Ser  Phe  Glu  Lys  Leu  Ala
                         3780                    3785                    3790

AAG  TTA  AAT  CTC  AGC  ATG  TCC  ACG  CTC  GGG  GTG  TGG  ACT  AGA  CAC  ACT      11784
Lys  Leu  Asn  Leu  Ser  Met  Ser  Thr  Leu  Gly  Val  Trp  Thr  Arg  His  Thr
                    3795                    3800                    3805

AGC  AAG  AGA  TTA  CTA  CAA  GAT  TGT  GTC  AAT  GTT  GGC  ACC  AAA  GAG  GGC      11832
Ser  Lys  Arg  Leu  Leu  Gln  Asp  Cys  Val  Asn  Val  Gly  Thr  Lys  Glu  Gly
          3810                    3815                    3820

AAC  TGG  CTG  GTC  AAT  GCA  GAC  AGA  CTA  GTG  AGT  AGT  AAG  ACA  GGA  AAC      11880
Asn  Trp  Leu  Val  Asn  Ala  Asp  Arg  Leu  Val  Ser  Ser  Lys  Thr  Gly  Asn
     3825                    3830                    3835

AGG  TAT  ATA  CCT  GGA  GAG  GGC  CAC  ACC  CTA  CAA  GGG  AAA  CAT  TAT  GAA      11928
Arg  Tyr  Ile  Pro  Gly  Glu  Gly  His  Thr  Leu  Gln  Gly  Lys  His  Tyr  Glu
3840                    3845                    3850                    3855

GAA  CTG  ATA  CTG  GCA  AGG  AAA  CCG  ATC  GGT  AAC  TTT  GAA  GGG  ACC  GAT      11976
Glu  Leu  Ile  Leu  Ala  Arg  Lys  Pro  Ile  Gly  Asn  Phe  Glu  Gly  Thr  Asp
                         3860                    3865                    3870

AGG  TAT  AAC  TTG  GGG  CCA  ATA  GTC  AAT  GTA  GTG  TTG  AGG  AGA  CTA  AAA      12024
Arg  Tyr  Asn  Leu  Gly  Pro  Ile  Val  Asn  Val  Val  Leu  Arg  Arg  Leu  Lys
                    3875                    3880                    3885

ATT  ATG  ATG  ATG  GCC  CTG  ATA  GGA  AGG  GGG  GTG  TGAGCATGGT  TGGCCCTTGA        12077
Ile  Met  Met  Met  Ala  Leu  Ile  Gly  Arg  Gly  Val
                         3890                    3895

TCGGGCCCTA  TCAGTAGAAC  CCTATTGTAA  ATAACATTAA  CTTATTAATT  ATTTAGATAC              12137

TATTATTTAT  TTATTTATTT  ATTTATTGAA  TGAGCAAGTA  CTGGTACAAA  CTACCTCATG              12197

TTACCACACT  ACACTCATTT  TAACAGCACT  TTAGCTGGAG  GGAAAACCCT  GACGTCCACA              12257

GTTGGACTAA  GGTAATTTCC  TAACGGC                                                    12284
```

( 2 ) INFORMATION FOR SEQ ID NO:2:

( i ) SEQUENCE CHARACTERISTICS:
        ( A ) LENGTH: 3898 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Leu  Asn  His  Phe  Glu  Leu  Leu  Tyr  Lys  Thr  Ser  Lys  Gln  Lys
  1                    5                         10                        15

Pro  Val  Gly  Val  Glu  Glu  Pro  Val  Tyr  Asp  Thr  Ala  Gly  Arg  Pro  Leu
               20                        25                        30
```

```
Phe Gly Asn Pro Ser Glu Val His Pro Gln Ser Thr Leu Lys Leu Pro
             35                  40                  45
His Asp Arg Gly Arg Gly Asp Ile Arg Thr Thr Leu Arg Asp Leu Pro
         50                  55                  60
Arg Lys Gly Asp Cys Arg Ser Gly Asn His Leu Gly Pro Val Ser Gly
 65                  70                  75                  80
Ile Tyr Ile Lys Pro Gly Pro Val Tyr Tyr Gln Asp Tyr Thr Gly Pro
                 85                  90                  95
Val Tyr His Arg Ala Pro Leu Glu Phe Phe Asp Glu Ala Gln Phe Cys
        100                 105                 110
Glu Val Thr Lys Arg Ile Gly Arg Val Thr Gly Ser Asp Gly Lys Leu
            115                 120                 125
Tyr His Ile Tyr Val Cys Val Asp Gly Cys Ile Leu Leu Lys Leu Ala
    130                 135                 140
Lys Arg Gly Thr Pro Arg Thr Leu Lys Trp Ile Arg Asn Phe Thr Asn
145                 150                 155                 160
Cys Pro Leu Trp Val Thr Ser Cys Ser Asp Asp Gly Ala Ser Gly Ser
                165                 170                 175
Lys Asp Lys Lys Pro Asp Arg Met Asn Lys Gly Lys Leu Lys Ile Ala
            180                 185                 190
Pro Arg Glu His Glu Lys Asp Ser Lys Thr Lys Pro Pro Asp Ala Thr
        195                 200                 205
Ile Val Val Glu Gly Val Lys Tyr Gln Ile Lys Lys Lys Gly Lys Val
    210                 215                 220
Lys Gly Lys Asn Thr Gln Asp Gly Leu Tyr His Asn Lys Asn Lys Pro
225                 230                 235                 240
Pro Glu Ser Arg Lys Lys Leu Glu Lys Ala Leu Leu Ala Trp Ala Val
                245                 250                 255
Ile Thr Ile Leu Leu Tyr Gln Pro Val Ala Ala Glu Asn Ile Thr Gln
            260                 265                 270
Trp Asn Leu Ser Asp Asn Gly Thr Asn Gly Ile Gln Arg Ala Met Tyr
        275                 280                 285
Leu Arg Gly Val Asn Arg Ser Leu His Gly Ile Trp Pro Glu Lys Ile
    290                 295                 300
Cys Lys Gly Val Pro Thr His Leu Ala Thr Asp Thr Glu Leu Lys Glu
305                 310                 315                 320
Ile Arg Gly Met Met Asp Ala Ser Glu Arg Thr Asn Tyr Thr Cys Cys
                325                 330                 335
Arg Leu Gln Arg His Glu Trp Asn Lys His Gly Trp Cys Asn Trp Tyr
            340                 345                 350
Asn Ile Asp Pro Trp Ile Gln Leu Met Asn Arg Thr Gln Thr Asn Leu
        355                 360                 365
Thr Glu Gly Pro Pro Asp Lys Glu Cys Ala Val Thr Cys Arg Tyr Asp
    370                 375                 380
Lys Asn Thr Asp Val Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
                405                 410                 415
Val Ile Glu Gly Pro Cys Asn Phe Asn Val Ser Val Glu Asp Ile Leu
            420                 425                 430
Tyr Gly Asp His Glu Cys Gly Ser Leu Leu Gln Asp Thr Ala Leu Tyr
        435                 440                 445
Leu Leu Asp Gly Met Thr Asn Thr Ile Glu Asn Ala Arg Gln Gly Ala
```

-continued

|     |     |     | 450 |     |     |     | 455 |     |     |     | 460 |     |     |     |
|---|---|---|---|---|---|---|---|---|---|---|---|---|---|---|
| Ala 465 | Arg | Val | Thr | Ser | Trp 470 | Leu | Gly | Arg | Gln | Leu 475 | Ser | Thr | Ala | Gly | Lys 480 |
| Lys | Leu | Glu | Arg | Arg 485 | Ser | Lys | Thr | Trp | Phe 490 | Gly | Ala | Tyr | Ala | Leu 495 | Ser |
| Pro | Tyr | Cys | Asn 500 | Val | Thr | Arg | Lys | Ile 505 | Gly | Tyr | Ile | Trp | Tyr 510 | Thr | Asn |
| Asn | Cys | Thr 515 | Pro | Ala | Cys | Leu | Pro 520 | Lys | Asn | Thr | Lys | Ile 525 | Ile | Gly | Pro |
| Gly | Lys 530 | Phe | Asp | Thr | Asn | Ala 535 | Glu | Asp | Gly | Lys | Ile 540 | Leu | His | Glu | Met |
| Gly 545 | Gly | His | Leu | Ser | Glu 550 | Phe | Leu | Leu | Leu | Ser 555 | Leu | Val | Ile | Leu | Ser 560 |
| Asp | Phe | Ala | Pro | Glu 565 | Thr | Ala | Ser | Thr | Leu 570 | Tyr | Leu | Ile | Leu | His 575 | Tyr |
| Ala | Ile | Pro | Gln 580 | Ser | His | Glu | Glu | Pro 585 | Glu | Gly | Cys | Asp | Thr 590 | Asn | Gln |
| Leu | Asn | Leu 595 | Thr | Val | Lys | Leu | Arg 600 | Thr | Glu | Asp | Val | Val 605 | Pro | Ser | Ser |
| Val | Trp 610 | Asn | Ile | Gly | Lys | Tyr 615 | Val | Cys | Val | Arg | Pro 620 | Asp | Trp | Trp | Pro |
| Tyr 625 | Glu | Thr | Lys | Val | Ala 630 | Leu | Leu | Phe | Glu | Glu 635 | Ala | Gly | Gln | Val | Ile 640 |
| Lys | Leu | Val | Leu | Arg 645 | Ala | Leu | Arg | Asp | Leu 650 | Thr | Arg | Val | Trp | Asn 655 | Ser |
| Ala | Ser | Thr | Thr 660 | Ala | Phe | Leu | Ile | Cys 665 | Leu | Ile | Lys | Val | Leu 670 | Arg | Gly |
| Gln | Val | Val 675 | Gln | Gly | Ile | Ile | Trp 680 | Leu | Leu | Leu | Val | Thr 685 | Gly | Ala | Gln |
| Gly | Arg 690 | Leu | Ala | Cys | Lys | Glu 695 | Asp | Tyr | Arg | Tyr | Ala 700 | Ile | Ser | Ser | Thr |
| Asn 705 | Glu | Ile | Gly | Leu | Leu 710 | Gly | Ala | Glu | Gly | Leu 715 | Thr | Thr | Thr | Trp | Lys 720 |
| Glu | Tyr | Ser | His | Gly 725 | Leu | Gln | Leu | Asp | Asp 730 | Gly | Thr | Val | Lys | Ala 735 | Val |
| Cys | Thr | Ala | Gly 740 | Ser | Phe | Lys | Val | Thr 745 | Ala | Leu | Asn | Val | Val 750 | Ser | Arg |
| Arg | Tyr | Leu 755 | Ala | Ser | Leu | His | Lys 760 | Arg | Ala | Leu | Pro | Thr 765 | Ser | Val | Thr |
| Phe | Glu 770 | Leu | Leu | Phe | Asp | Gly 775 | Thr | Asn | Pro | Ala | Ile 780 | Glu | Glu | Met | Asp |
| Asp 785 | Asp | Phe | Gly | Phe | Gly 790 | Leu | Cys | Pro | Phe | Asp 795 | Thr | Ser | Pro | Val | Ile 800 |
| Lys | Gly | Lys | Tyr | Asn 805 | Thr | Thr | Leu | Leu | Asn 810 | Gly | Ser | Ala | Phe | Tyr 815 | Leu |
| Val | Cys | Pro | Ile 820 | Gly | Trp | Thr | Gly | Val 825 | Val | Glu | Cys | Thr | Ala 830 | Val | Ser |
| Pro | Thr | Thr 835 | Leu | Arg | Thr | Glu | Val 840 | Val | Lys | Thr | Phe | Arg 845 | Arg | Asp | Lys |
| Pro | Phe 850 | Pro | His | Arg | Val | Asp 855 | Cys | Val | Thr | Thr | Ile 860 | Val | Glu | Lys | Glu |
| Asp 865 | Leu | Phe | His | Cys | Lys 870 | Leu | Gly | Gly | Asn | Trp 875 | Thr | Cys | Val | Lys | Gly 880 |

```
Asp Pro Val Thr Tyr Lys Gly Gly Gln Val Lys Gln Cys Arg Trp Cys
            885                 890                 895
Gly Phe Glu Phe Lys Glu Pro Tyr Gly Leu Pro His Tyr Pro Ile Gly
            900                 905                 910
Lys Cys Ile Leu Thr Asn Glu Thr Gly Tyr Arg Val Val Asp Ser Thr
            915                 920                 925
Asp Cys Asn Arg Asp Gly Val Val Ile Ser Thr Glu Gly Glu His Glu
            930                 935                 940
Cys Leu Ile Gly Asn Thr Thr Val Lys Val His Ala Leu Asp Glu Arg
945                 950                 955                 960
Leu Gly Pro Met Pro Cys Arg Pro Lys Glu Ile Val Ser Ser Glu Gly
                965                 970                 975
Pro Val Arg Lys Thr Ser Cys Thr Phe Asn Tyr Thr Lys Thr Leu Arg
            980                 985                 990
Asn Lys Tyr Tyr Glu Pro Arg Asp Ser Tyr Phe Gln Gln Tyr Met Leu
            995                 1000                1005
Lys Gly Glu Tyr Gln Tyr Trp Phe Asn Leu Asp Val Thr Asp His His
            1010                1015                1020
Thr Asp Tyr Phe Ala Glu Phe Val Val Leu Val Val Ala Leu Leu Leu
1025                1030                1035                1040
Gly Gly Arg Tyr Val Leu Trp Leu Ile Val Thr Tyr Ile Ile Leu Thr
            1045                1050                1055
Glu Gln Leu Ala Ala Gly Leu Gln Leu Gly Gln Gly Glu Val Val Leu
            1060                1065                1070
Ile Gly Asn Leu Ile Thr His Thr Asp Asn Glu Val Val Val Tyr Phe
            1075                1080                1085
Leu Leu Leu Tyr Leu Val Ile Arg Asp Glu Pro Ile Lys Lys Trp Ile
            1090                1095                1100
Leu Leu Leu Phe His Ala Met Thr Asn Asn Pro Val Lys Thr Ile Thr
1105                1110                1115                1120
Val Ala Leu Leu Met Ile Ser Gly Val Ala Lys Gly Gly Lys Ile Asp
            1125                1130                1135
Gly Gly Trp Gln Arg Gln Pro Val Thr Ser Phe Asp Ile Gln Leu Ala
            1140                1145                1150
Leu Ala Val Val Val Val Val Val Met Leu Leu Ala Lys Arg Asp Pro
            1155                1160                1165
Thr Thr Phe Pro Leu Val Ile Thr Val Ala Thr Leu Arg Thr Ala Lys
            1170                1175                1180
Ile Thr Asn Gly Phe Ser Thr Asp Leu Val Ile Ala Thr Val Ser Ala
1185                1190                1195                1200
Ala Leu Leu Thr Trp Thr Tyr Ile Ser Asp Tyr Tyr Lys Tyr Lys Thr
            1205                1210                1215
Trp Leu Gln Tyr Leu Val Ser Thr Val Thr Gly Ile Phe Leu Ile Arg
            1220                1225                1230
Val Leu Lys Gly Ile Gly Glu Leu Asp Leu His Ala Pro Thr Leu Pro
            1235                1240                1245
Ser His Arg Pro Leu Phe Tyr Ile Leu Val Tyr Leu Ile Ser Thr Ala
            1250                1255                1260
Val Val Thr Arg Trp Asn Leu Asp Val Ala Gly Leu Leu Leu Gln Cys
1265                1270                1275                1280
Val Pro Thr Leu Leu Met Val Phe Thr Met Trp Ala Asp Ile Leu Thr
            1285                1290                1295
Leu Ile Leu Ile Leu Pro Thr Tyr Glu Leu Thr Lys Leu Tyr Tyr Leu
            1300                1305                1310
```

```
Lys Glu Val Lys Ile Gly Ala Glu Arg Gly Trp Leu Trp Lys Thr Asn
         1315                1320                1325
Tyr Lys Arg Val Asn Asp Ile Tyr Glu Val Asp Gln Thr Ser Glu Gly
         1330                1335                1340
Val Tyr Leu Phe Pro Ser Lys Gln Arg Thr Ser Ala Ile Thr Ser Thr
1345                1350                1355                1360
Met Leu Pro Leu Ile Lys Ala Ile Leu Ile Ser Cys Ile Ser Asn Lys
             1365                1370                1375
Trp Gln Leu Ile Tyr Leu Leu Tyr Leu Ile Phe Glu Val Ser Tyr Tyr
             1380                1385                1390
Leu His Lys Lys Val Ile Asp Glu Ile Ala Gly Gly Thr Asn Phe Val
             1395                1400                1405
Ser Arg Leu Val Ala Ala Leu Ile Glu Val Asn Trp Ala Phe Asp Asn
         1410                1415                1420
Glu Glu Val Lys Gly Leu Lys Lys Phe Phe Leu Leu Ser Ser Arg Val
1425                1430                1435                1440
Lys Glu Leu Ile Ile Lys His Lys Val Arg Asn Glu Val Val Val Arg
             1445                1450                1455
Trp Phe Gly Asp Glu Glu Ile Tyr Gly Met Pro Lys Leu Ile Gly Leu
             1460                1465                1470
Val Lys Ala Ala Thr Leu Ser Arg Asn Lys His Cys Met Leu Cys Thr
         1475                1480                1485
Val Cys Glu Asp Arg Asp Trp Arg Gly Glu Thr Cys Pro Lys Cys Gly
         1490                1495                1500
Arg Phe Gly Pro Pro Val Val Cys Gly Met Thr Leu Ala Asp Phe Glu
1505                1510                1515                1520
Glu Lys His Tyr Lys Arg Ile Phe Ile Arg Glu Asp Gln Ser Gly Gly
             1525                1530                1535
Pro Leu Arg Glu Glu His Ala Gly Tyr Leu Gln Tyr Lys Ala Arg Gly
         1540                1545                1550
Gln Leu Phe Leu Arg Asn Leu Pro Val Leu Ala Thr Lys Val Lys Met
         1555                1560                1565
Leu Leu Val Gly Asn Leu Gly Thr Glu Ile Gly Asp Leu Glu His Leu
1570                1575                1580
Gly Trp Val Leu Arg Gly Pro Ala Val Cys Lys Lys Val Thr Glu His
1585                1590                1595                1600
Glu Arg Cys Thr Thr Ser Ile Met Asp Lys Leu Thr Ala Phe Phe Gly
             1605                1610                1615
Val Met Pro Arg Gly Thr Thr Pro Arg Ala Pro Val Arg Phe Pro Thr
             1620                1625                1630
Ser Leu Leu Lys Ile Arg Arg Gly Leu Glu Thr Gly Trp Ala Tyr Thr
             1635                1640                1645
His Gln Gly Gly Ile Ser Ser Val Asp His Val Thr Cys Gly Lys Asp
         1650                1655                1660
Leu Leu Val Cys Asp Thr Met Gly Arg Thr Arg Val Val Cys Gln Ser
1665                1670                1675                1680
Asn Asn Lys Met Thr Asp Glu Ser Glu Tyr Gly Val Lys Thr Asp Ser
             1685                1690                1695
Gly Cys Pro Glu Gly Ala Arg Cys Tyr Val Phe Asn Pro Glu Ala Val
             1700                1705                1710
Asn Ile Ser Gly Thr Lys Gly Ala Met Val His Leu Gln Lys Thr Gly
             1715                1720                1725
Gly Glu Phe Thr Cys Val Thr Ala Ser Gly Thr Pro Ala Phe Phe Asp
```

```
                1730                      1735                      1740
Leu  Lys  Asn  Leu  Lys  Gly  Trp  Ser  Gly  Leu  Pro  Ile  Phe  Glu  Ala  Ser
1745                      1750                      1755                      1760

Ser  Gly  Arg  Val  Val  Gly  Arg  Val  Lys  Val  Gly  Lys  Asn  Glu  Asp  Ser
                     1765                      1770                      1775

Lys  Pro  Thr  Lys  Leu  Met  Ser  Gly  Ile  Gln  Thr  Val  Ser  Lys  Ser  Ala
                     1780                      1785                      1790

Thr  Asp  Leu  Thr  Glu  Met  Val  Lys  Lys  Ile  Thr  Thr  Met  Asn  Arg  Gly
                1795                      1800                      1805

Glu  Phe  Arg  Gln  Ile  Thr  Leu  Ala  Thr  Gly  Ala  Gly  Lys  Thr  Thr  Glu
                1810                      1815                      1820

Leu  Pro  Arg  Ser  Val  Ile  Glu  Glu  Ile  Gly  Arg  His  Lys  Arg  Val  Leu
1825                      1830                      1835                      1840

Val  Leu  Ile  Pro  Leu  Arg  Ala  Ala  Ala  Glu  Ser  Val  Tyr  Gln  Tyr  Met
                     1845                      1850                      1855

Arg  Gln  Lys  His  Pro  Ser  Ile  Ala  Phe  Asn  Leu  Arg  Ile  Gly  Glu  Met
                     1860                      1865                      1870

Lys  Glu  Gly  Asp  Met  Ala  Thr  Gly  Ile  Thr  Tyr  Ala  Ser  Tyr  Gly  Tyr
                     1875                      1880                      1885

Phe  Cys  Gln  Met  Ser  Gln  Pro  Lys  Leu  Arg  Ala  Ala  Met  Val  Glu  Tyr
                     1890                      1895                      1900

Ser  Phe  Ile  Phe  Leu  Asp  Glu  Tyr  His  Cys  Ala  Thr  Pro  Glu  Gln  Leu
1905                      1910                      1915                      1920

Ala  Ile  Met  Gly  Lys  Ile  His  Arg  Phe  Ser  Glu  Asn  Leu  Arg  Val  Val
                     1925                      1930                      1935

Ala  Met  Thr  Ala  Thr  Pro  Ala  Gly  Thr  Val  Thr  Thr  Thr  Gly  Gln  Lys
                     1940                      1945                      1950

His  Pro  Ile  Glu  Glu  Phe  Ile  Ala  Pro  Glu  Val  Met  Lys  Gly  Glu  Asp
                     1955                      1960                      1965

Leu  Gly  Ser  Glu  Tyr  Leu  Asp  Ile  Ala  Gly  Leu  Lys  Ile  Pro  Val  Glu
                     1970                      1975                      1980

Glu  Met  Lys  Asn  Asn  Met  Leu  Val  Phe  Val  Pro  Thr  Arg  Asn  Met  Ala
1985                      1990                      1995                      2000

Val  Glu  Ala  Ala  Lys  Lys  Leu  Lys  Ala  Lys  Gly  Tyr  Asn  Ser  Gly  Tyr
                     2005                      2010                      2015

Tyr  Tyr  Ser  Gly  Glu  Asp  Pro  Ser  Asn  Leu  Arg  Val  Val  Thr  Ser  Gln
                     2020                      2025                      2030

Ser  Pro  Tyr  Val  Val  Val  Ala  Thr  Asn  Ala  Ile  Glu  Ser  Gly  Val  Thr
                     2035                      2040                      2045

Leu  Pro  Asp  Leu  Asp  Val  Val  Val  Asp  Thr  Gly  Leu  Lys  Cys  Glu  Lys
2050                      2055                      2060

Arg  Ile  Arg  Leu  Ser  Pro  Lys  Met  Pro  Phe  Ile  Val  Thr  Gly  Leu  Lys
2065                      2070                      2075                      2080

Arg  Met  Ala  Val  Thr  Ile  Gly  Glu  Gln  Ala  Gln  Arg  Arg  Gly  Arg  Val
                     2085                      2090                      2095

Gly  Arg  Val  Lys  Pro  Gly  Arg  Tyr  Tyr  Arg  Ser  Gln  Glu  Thr  Pro  Val
                     2100                      2105                      2110

Gly  Ser  Lys  Asp  Tyr  His  Tyr  Asp  Leu  Leu  Gln  Ala  Gln  Arg  Tyr  Gly
                     2115                      2120                      2125

Ile  Glu  Asp  Gly  Ile  Asn  Ile  Thr  Lys  Ser  Phe  Arg  Glu  Met  Asn  Tyr
                     2130                      2135                      2140

Asp  Trp  Ser  Leu  Tyr  Glu  Glu  Asp  Ser  Leu  Met  Ile  Thr  Gln  Leu  Glu
2145                      2150                      2155                      2160
```

```
Ile Leu Asn Asn Leu Leu Ile Ser Glu Glu Leu Pro Met Ala Val Lys
                2165                2170                2175
Asn Ile Met Ala Arg Thr Asp His Pro Glu Pro Ile Gln Leu Ala Tyr
                2180                2185                2190
Asn Ser Tyr Glu Thr Gln Val Pro Val Leu Phe Pro Lys Ile Arg Asn
                2195                2200                2205
Gly Glu Val Thr Asp Thr Tyr Asp Asn Tyr Thr Phe Leu Asn Ala Arg
    2210                2215                2220
Lys Leu Gly Asp Asp Val Pro Pro Tyr Val Tyr Ala Thr Glu Asp Glu
2225                2230                2235                2240
Asp Leu Ala Val Glu Leu Leu Gly Leu Asp Trp Pro Asp Pro Gly Asn
                2245                2250                2255
Gln Gly Thr Val Glu Ala Gly Arg Ala Leu Lys Gln Val Val Gly Leu
                2260                2265                2270
Ser Thr Ala Glu Asn Ala Leu Leu Val Ala Leu Phe Gly Tyr Val Gly
                2275                2280                2285
Tyr Gln Ala Leu Ser Lys Arg His Ile Pro Val Val Thr Asp Ile Tyr
                2290                2295                2300
Ser Val Glu Asp His Arg Leu Glu Asp Thr Thr His Leu Gln Tyr Ala
2305                2310                2315                2320
Pro Asn Ala Ile Lys Thr Glu Gly Lys Glu Thr Glu Leu Lys Glu Leu
                2325                2330                2335
Ala Gln Gly Asp Val Gln Arg Cys Val Glu Ala Val Thr Asn Tyr Ala
                2340                2345                2350
Arg Glu Gly Ile Gln Phe Met Lys Ser Gln Ala Leu Lys Val Arg Glu
                2355                2360                2365
Thr Pro Thr Tyr Lys Glu Thr Met Asn Thr Val Ala Asp Tyr Val Lys
                2370                2375                2380
Lys Phe Ile Glu Ala Leu Thr Asp Ser Lys Glu Asp Ile Ile Lys Tyr
2385                2390                2395                2400
Gly Leu Trp Gly Ala His Thr Ala Leu Tyr Lys Ser Ile Gly Ala Arg
                2405                2410                2415
Leu Gly His Glu Thr Ala Phe Ala Thr Leu Val Val Lys Trp Leu Ala
                2420                2425                2430
Phe Gly Gly Glu Ser Ile Ser Asp His Ile Lys Gln Ala Ala Thr Asp
                2435                2440                2445
Leu Val Val Tyr Tyr Ile Ile Asn Arg Pro Gln Phe Pro Gly Asp Thr
                2450                2455                2460
Glu Thr Gln Gln Glu Gly Arg Lys Phe Val Ala Ser Leu Leu Val Ser
2465                2470                2475                2480
Ala Leu Ala Thr Tyr Thr Tyr Lys Ser Trp Asn Tyr Asn Asn Leu Ser
                2485                2490                2495
Lys Ile Val Glu Pro Ala Leu Ala Thr Leu Pro Tyr Ala Ala Lys Ala
                2500                2505                2510
Leu Lys Leu Phe Ala Pro Thr Arg Leu Glu Ser Val Val Ile Leu Ser
                2515                2520                2525
Thr Ala Ile Tyr Lys Thr Tyr Leu Ser Ile Arg Arg Gly Lys Ser Asp
                2530                2535                2540
Gly Leu Leu Gly Thr Gly Val Ser Ala Ala Met Glu Ile Met Ser Gln
2545                2550                2555                2560
Asn Pro Val Ser Val Gly Ile Ala Val Met Leu Gly Val Gly Ala Val
                2565                2570                2575
Ala Ala His Asn Ala Ile Glu Ala Ser Glu Gln Lys Arg Thr Leu Leu
                2580                2585                2590
```

```
Met  Lys  Val  Phe  Val  Lys  Asn  Phe  Leu  Asp  Gln  Ala  Ala  Thr  Asp  Glu
              2595                2600                2605

Leu  Val  Lys  Glu  Ser  Pro  Glu  Lys  Ile  Ile  Met  Ala  Leu  Phe  Glu  Ala
              2610                2615                2620

Val  Gln  Thr  Val  Gly  Asn  Pro  Leu  Arg  Leu  Val  Tyr  His  Leu  Tyr  Gly
2625                2630                2635                          2640

Val  Phe  Tyr  Lys  Gly  Trp  Glu  Ala  Lys  Glu  Leu  Ala  Gln  Arg  Thr  Ala
              2645                2650                          2655

Gly  Arg  Asn  Leu  Phe  Thr  Leu  Ile  Met  Phe  Glu  Ala  Val  Glu  Leu  Leu
              2660                2665                2670

Gly  Val  Asp  Ser  Glu  Gly  Lys  Ile  Arg  Gln  Leu  Ser  Ser  Asn  Tyr  Ile
              2675                2680                2685

Leu  Glu  Leu  Leu  Tyr  Lys  Phe  Arg  Asp  Asn  Ile  Lys  Ser  Ser  Val  Arg
              2690                2695                2700

Glu  Ile  Ala  Ile  Ser  Trp  Ala  Pro  Ala  Pro  Phe  Ser  Cys  Asp  Trp  Thr
2705                2710                2715                          2720

Pro  Thr  Asp  Asp  Arg  Ile  Gly  Leu  Pro  His  Asp  Asn  Tyr  Leu  Arg  Val
              2725                2730                2735

Glu  Thr  Lys  Cys  Pro  Cys  Gly  Tyr  Arg  Met  Lys  Ala  Val  Lys  Asn  Cys
              2740                2745                2750

Ala  Gly  Glu  Leu  Arg  Leu  Leu  Glu  Gly  Gly  Ser  Phe  Leu  Cys  Arg
              2755                2760                2765

Asn  Lys  Phe  Gly  Arg  Gly  Ser  Gln  Asn  Tyr  Arg  Val  Thr  Lys  Tyr  Tyr
2770                2775                2780

Asp  Asp  Asn  Leu  Ser  Glu  Ile  Lys  Pro  Val  Ile  Arg  Met  Glu  Gly  His
2785                2790                2795                          2800

Val  Glu  Leu  Tyr  Tyr  Lys  Gly  Ala  Thr  Ile  Lys  Leu  Asp  Phe  Asn  Asn
              2805                2810                2815

Ser  Lys  Thr  Val  Leu  Ala  Thr  Asp  Lys  Trp  Glu  Val  Asp  His  Ser  Thr
              2820                2825                2830

Leu  Val  Arg  Ala  Leu  Lys  Arg  Tyr  Thr  Gly  Ala  Gly  Tyr  Arg  Gly  Ala
              2835                2840                2845

Tyr  Leu  Gly  Glu  Lys  Pro  Asn  His  Lys  His  Leu  Ile  Gln  Arg  Asp  Cys
              2850                2855                2860

Ala  Thr  Ile  Thr  Lys  Asp  Lys  Val  Cys  Phe  Ile  Lys  Met  Lys  Arg  Gly
2865                2870                2875                          2880

Cys  Ala  Phe  Thr  Tyr  Asp  Leu  Ser  Leu  His  Asn  Leu  Thr  Arg  Leu  Ile
              2885                2890                2895

Glu  Leu  Val  His  Lys  Asn  Asn  Leu  Glu  Asp  Arg  Glu  Ile  Pro  Ala  Val
              2900                2905                2910

Thr  Val  Thr  Thr  Trp  Leu  Ala  Tyr  Thr  Phe  Val  Asn  Glu  Asp  Ile  Gly
              2915                2920                2925

Thr  Ile  Lys  Pro  Thr  Phe  Gly  Glu  Lys  Val  Thr  Pro  Glu  Lys  Gln  Glu
              2930                2935                2940

Glu  Val  Val  Leu  Gln  Pro  Ala  Val  Val  Val  Asp  Thr  Thr  Asp  Val  Ala
2945                2950                2955                          2960

Val  Thr  Val  Val  Gly  Glu  Thr  Ser  Thr  Met  Thr  Thr  Gly  Glu  Thr  Pro
              2965                2970                2975

Thr  Thr  Phe  Thr  Ser  Leu  Gly  Ser  Asp  Ser  Lys  Val  Arg  Gln  Val  Leu
              2980                2985                2990

Lys  Leu  Gly  Val  Asp  Asp  Gly  Gln  Tyr  Pro  Gly  Pro  Asn  Gln  Gln  Arg
              2995                3000                3005

Ala  Ser  Leu  Leu  Glu  Ala  Ile  Gln  Gly  Val  Asp  Glu  Arg  Pro  Ser  Val
```

-continued

|  | 3010 |  |  |  | 3015 |  |  |  | 3020 |  |  |
|---|---|---|---|---|---|---|---|---|---|---|---|

Leu Ile Leu Gly Ser Asp Lys Ala Thr Ser Asn Arg Val Lys Thr Ala
3025                3030                    3035                    3040

Lys Asn Val Lys Ile Tyr Arg Ser Arg Asp Pro Leu Glu Leu Arg Glu
      3045                    3050                    3055

Met Met Lys Arg Gly Lys Ile Leu Val Val Ala Leu Ser Arg Val Asp
      3060                    3065                    3070

Thr Ala Leu Leu Lys Phe Val Asp Tyr Lys Gly Thr Phe Leu Thr Arg
      3075                    3080                    3085

Glu Thr Leu Glu Ala Leu Ser Leu Gly Lys Pro Lys Lys Arg Asp Ile
      3090                    3095                    3100

Thr Lys Ala Glu Ala Gln Trp Leu Leu Arg Leu Glu Asp Gln Ile Glu
3105                3110                    3115                    3120

Glu Leu Pro Asp Trp Phe Ala Ala Lys Glu Pro Ile Phe Leu Glu Ala
      3125                    3130                    3135

Asn Ile Lys Arg Asp Lys Tyr His Leu Val Gly Asp Ile Ala Thr Ile
      3140                    3145                    3150

Lys Glu Lys Ala Lys Gln Leu Gly Ala Thr Asp Ser Thr Lys Ile Ser
      3155                    3160                    3165

Lys Glu Val Gly Ala Lys Val Tyr Ser Met Lys Leu Ser Asn Trp Val
      3170                    3175                    3180

Ile Gln Glu Glu Asn Lys Gln Gly Ser Leu Ala Pro Leu Phe Glu Glu
3185                3190                    3195                    3200

Leu Leu Gln Gln Cys Pro Pro Gly Gly Gln Asn Lys Thr Thr His Met
            3205                    3210                    3215

Val Ser Ala Tyr Gln Leu Ala Gln Gly Asn Trp Val Pro Val Ser Cys
      3220                    3225                    3230

His Val Phe Met Gly Thr Ile Pro Ala Arg Arg Thr Lys Thr His Pro
      3235                    3240                    3245

Tyr Glu Ala Tyr Val Lys Leu Arg Glu Leu Val Asp Glu His Lys Met
      3250                    3255                    3260

Lys Ala Leu Cys Gly Gly Ser Gly Leu Ser Lys His Asn Glu Trp Val
3265                3270                    3275                    3280

Ile Gly Lys Val Lys Tyr Gln Gly Asn Leu Arg Thr Lys His Met Leu
            3285                    3290                    3295

Asn Pro Gly Lys Val Ala Glu Gln Leu His Arg Glu Gly Tyr Arg His
      3300                    3305                    3310

Asn Val Tyr Asn Lys Thr Ile Gly Ser Val Met Thr Ala Thr Gly Ile
      3315                    3320                    3325

Arg Leu Glu Lys Leu Pro Val Val Arg Ala Gln Thr Asp Thr Thr Asn
3330                3335                    3340

Phe His Gln Ala Ile Arg Asp Lys Ile Asp Lys Glu Glu Asn Leu Gln
3345                3350                    3355                    3360

Thr Pro Gly Leu His Lys Lys Leu Met Glu Val Phe Asn Ala Leu Lys
            3365                    3370                    3375

Arg Pro Glu Leu Glu Ala Ser Tyr Asp Ala Val Asp Trp Glu Glu Leu
      3380                    3385                    3390

Glu Arg Gly Ile Asn Arg Lys Gly Ala Ala Gly Phe Phe Glu Arg Lys
      3395                    3400                    3405

Asn Ile Gly Glu Val Leu Asp Ser Glu Lys Asn Lys Val Glu Glu Val
      3410                    3415                    3420

Ile Asp Ser Leu Lys Lys Gly Arg Asn Ile Arg Tyr Tyr Glu Thr Ala
3425                3430                    3435                    3440

-continued

```
Ile  Pro  Lys  Asn  Glu  Lys  Arg  Asp  Val  Asn  Asp  Asp  Trp  Thr  Ala  Gly
               3445                3450                     3455

Asp  Phe  Val  Asp  Glu  Lys  Lys  Pro  Arg  Val  Ile  Gln  Tyr  Pro  Glu  Ala
               3460                3465                     3470

Lys  Thr  Arg  Leu  Ala  Ile  Thr  Lys  Val  Met  Tyr  Lys  Trp  Val  Lys  Gln
               3475                3480                     3485

Lys  Pro  Val  Val  Ile  Pro  Gly  Tyr  Glu  Gly  Lys  Thr  Pro  Leu  Phe  Gln
               3490                3495                     3500

Ile  Phe  Asp  Lys  Val  Lys  Lys  Glu  Trp  Asp  Gln  Phe  Gln  Asn  Pro  Val
3505                3510                3515                          3520

Ala  Val  Ser  Phe  Asp  Thr  Lys  Ala  Trp  Asp  Thr  Gln  Val  Thr  Thr  Arg
               3525                3530                     3535

Asp  Leu  Glu  Leu  Ile  Arg  Asp  Ile  Gln  Lys  Phe  Tyr  Phe  Lys  Lys  Lys
               3540                3545                     3550

Trp  His  Lys  Phe  Ile  Asp  Thr  Leu  Thr  Lys  His  Met  Ser  Glu  Val  Pro
               3555                3560                     3565

Val  Ile  Ser  Ala  Asp  Gly  Glu  Val  Tyr  Ile  Arg  Lys  Gly  Gln  Arg  Gly
               3570                3575                     3580

Ser  Gly  Gln  Pro  Asp  Thr  Ser  Ala  Gly  Asn  Ser  Met  Leu  Asn  Val  Leu
3585                3590                3595                          3600

Thr  Met  Val  Tyr  Ala  Phe  Cys  Glu  Ala  Thr  Gly  Val  Pro  Tyr  Lys  Ser
               3605                3610                     3615

Phe  Asp  Arg  Val  Ala  Lys  Ile  His  Val  Cys  Gly  Asp  Asp  Gly  Phe  Leu
               3620                3625                     3630

Ile  Thr  Glu  Arg  Ala  Leu  Gly  Glu  Lys  Phe  Ala  Ser  Lys  Gly  Val  Gln
               3635                3640                     3645

Ile  Leu  Tyr  Glu  Ala  Gly  Lys  Pro  Gln  Lys  Ile  Thr  Glu  Gly  Asp  Lys
               3650                3655                     3660

Met  Lys  Val  Ala  Tyr  Gln  Phe  Asp  Asp  Ile  Glu  Phe  Cys  Ser  His  Thr
3665                3670                3675                          3680

Pro  Val  Gln  Val  Arg  Trp  Ser  Asp  Asn  Thr  Ser  Ser  Tyr  Met  Pro  Gly
               3685                3690                     3695

Arg  Asn  Thr  Thr  Thr  Ile  Leu  Ala  Lys  Met  Ala  Thr  Arg  Leu  Asp  Ser
               3700                3705                     3710

Ser  Gly  Glu  Arg  Gly  Thr  Ile  Ala  Tyr  Glu  Lys  Ala  Val  Ala  Phe  Ser
               3715                3720                     3725

Phe  Leu  Leu  Met  Tyr  Ser  Trp  Asn  Pro  Leu  Ile  Arg  Arg  Ile  Cys  Leu
               3730                3735                     3740

Leu  Val  Leu  Ser  Thr  Glu  Leu  Gln  Val  Arg  Pro  Gly  Lys  Ser  Thr  Thr
3745                3750                3755                          3760

Tyr  Tyr  Tyr  Glu  Gly  Asp  Pro  Ile  Ser  Ala  Tyr  Lys  Glu  Val  Ile  Gly
               3765                3770                     3775

His  Asn  Leu  Phe  Asp  Leu  Lys  Arg  Thr  Ser  Phe  Glu  Lys  Leu  Ala  Lys
               3780                3785                     3790

Leu  Asn  Leu  Ser  Met  Ser  Thr  Leu  Gly  Val  Trp  Thr  Arg  His  Thr  Ser
               3795                3800                     3805

Lys  Arg  Leu  Leu  Gln  Asp  Cys  Val  Asn  Val  Gly  Thr  Lys  Glu  Gly  Asn
               3810                3815                     3820

Trp  Leu  Val  Asn  Ala  Asp  Arg  Leu  Val  Ser  Ser  Lys  Thr  Gly  Asn  Arg
3825                3830                3835                          3840

Tyr  Ile  Pro  Gly  Glu  Gly  His  Thr  Leu  Gln  Gly  Lys  His  Tyr  Glu  Glu
               3845                3850                     3855

Leu  Ile  Leu  Ala  Arg  Lys  Pro  Ile  Gly  Asn  Phe  Glu  Gly  Thr  Asp  Arg
               3860                3865                     3870
```

Tyr Asn Leu Gly Pro Ile Val Asn Val Val Leu Arg Arg Leu Lys Ile
            3875                3880                    3885
Met Met Met Ala Leu Ile Gly Arg Gly Val
            3890                3895

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 1..33
        ( D ) OTHER INFORMATION: /label= primer_1

( x i ) SEQUENCE DESCRIPTION: SEQ ID NO:3:

CCTACTAACC ACGTTAAGTG CTGTGACTTT AAA        33

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 1..39
        ( D ) OTHER INFORMATION: /label= primer_2

( x i ) SEQUENCE DESCRIPTION: SEQ ID NO:4:

TTCTGTTCTC AAGGTTGTGG GGCTCACTGC TGTGCACTC        39

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 1..16
        ( D ) OTHER INFORMATION: /label= Adaptor_1
            / note="Upper strand of Bam HI - Hinf I adaptor,
            containing ATG at 364-366"

( x i ) SEQUENCE DESCRIPTION: SEQ ID NO:5:

GATCCACCAT GGAGTT        16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 1..16
        ( D ) OTHER INFORMATION: /label= Adaptor_2
            / note="Lower strand of Bam HI - Hinf I adaptor,
            containing ATG at 364-366"

( x i ) SEQUENCE DESCRIPTION: SEQ ID NO:6:

GTGGTACCTC AACTTA  16

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ix) FEATURE:
        (A) NAME/KEY: -
        (B) LOCATION: 1..10
        (D) OTHER INFORMATION: /label= Adaptor_3
            / note="Double stranded Stu I - Eco RI blunt adaptor"

(xi) SEQUENCE DESCRIPTION: SEQ ID NO:7:

GCCTGAATTC  10

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..21
        (D) OTHER INFORMATION: /label= Adaptor_4
            / note="Upper strand of Bgl II - BamH I adaptor"

(xi) SEQUENCE DESCRIPTION: SEQ ID NO:8:

GATCCACCAT GGGGGCCCTG T  21

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..14
        (D) OTHER INFORMATION: /label= Adaptor_5
            / note="Lower strand of Bgl II - BamH I adaptor"

(xi) SEQUENCE DESCRIPTION: SEQ ID NO:9:

GTGGTACCCC CGGG  14

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..15
        (D) OTHER INFORMATION: /label= Adaptor_6
            / note="Upper strand of Ban I - Eco R I adaptor"

(xi) SEQUENCE DESCRIPTION: SEQ ID NO:10:

GTGCCTATGC CTGAG  15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 1..15
        ( D ) OTHER INFORMATION: /label= Adaptor_7
        / note="Lower strand of Ban I - Eco R I adaptor"

( x i ) SEQUENCE DESCRIPTION: SEQ ID NO:11:

GATACGGACT CTTAA      15

( 2 ) INFORMATION FOR SEQ ID NO:12:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: lambda gt11 clone ( i x ) FEATURE:
        ( A ) NAME/KEY: CDS
        ( B ) LOCATION: 1..300
        ( D ) OTHER INFORMATION: /note="Part of 0.8 kb insert of
        Lambda gt11"

( x i ) SEQUENCE DESCRIPTION: SEQ ID NO:12:

```
AGT  GAC  AAC  GGC  ACT  AAT  GGT  ATT  CAG  CGA  GCC  ATG  TAT  CTT  AGA  GGG     48
Ser  Asp  Asn  Gly  Thr  Asn  Gly  Ile  Gln  Arg  Ala  Met  Tyr  Leu  Arg  Gly
 1                   5                   10                  15

GTT  AAC  AGG  AGC  TTA  CAT  GGG  ATC  TGG  CCC  GAG  AAA  ATA  TGC  AAG  GGG     96
Val  Asn  Arg  Ser  Leu  His  Gly  Ile  Trp  Pro  Glu  Lys  Ile  Cys  Lys  Gly
                     20                  25                  30

GTC  CCC  ACT  CAT  CTG  GCC  ACT  GAC  ACG  GAA  CTG  AAA  GAG  ATA  CGC  GGG    144
Val  Pro  Thr  His  Leu  Ala  Thr  Asp  Thr  Glu  Leu  Lys  Glu  Ile  Arg  Gly
           35                       40                  45

ATG  ATG  GAT  GCC  AGC  GAG  AGG  ACA  AAC  TAT  ACG  TGC  TGT  AGG  TTA  CAA    192
Met  Met  Asp  Ala  Ser  Glu  Arg  Thr  Asn  Tyr  Thr  Cys  Cys  Arg  Leu  Gln
      50                  55                       60

AGA  CAT  GAA  TGG  AAC  AAA  CAT  GGA  TGG  TGT  AAC  TGG  TAC  AAC  ATA  GAC    240
Arg  His  Glu  Trp  Asn  Lys  His  Gly  Trp  Cys  Asn  Trp  Tyr  Asn  Ile  Asp
 65                       70                  75                       80

CCT  TGG  ATT  CAG  TTA  ATG  AAC  AGG  ACC  CAA  ACA  AAT  TTG  ACA  GAA  GGC    288
Pro  Trp  Ile  Gln  Leu  Met  Asn  Arg  Thr  Gln  Thr  Asn  Leu  Thr  Glu  Gly
                     85                  90                  95

CCT  CCA  GAT  AAG                                                                 300
Pro  Pro  Asp  Lys
               100
```

( 2 ) INFORMATION FOR SEQ ID NO:13:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Ser 1 | Asp | Asn | Gly | Thr 5 | Asn | Gly | Ile | Gln | Arg 10 | Ala | Met | Tyr | Leu | Arg 15 | Gly |
| Val | Asn | Arg | Ser 20 | Leu | His | Gly | Ile | Trp 25 | Pro | Glu | Lys | Ile | Cys 30 | Lys | Gly |
| Val | Pro | Thr 35 | His | Leu | Ala | Thr | Asp 40 | Thr | Glu | Leu | Lys | Glu 45 | Ile | Arg | Gly |
| Met | Met 50 | Asp | Ala | Ser | Glu | Arg 55 | Thr | Asn | Tyr | Thr | Cys 60 | Cys | Arg | Leu | Gln |
| Arg 65 | His | Glu | Trp | Asn | Lys 70 | His | Gly | Trp | Cys | Asn 75 | Trp | Tyr | Asn | Ile | Asp 80 |
| Pro | Trp | Ile | Gln | Leu 85 | Met | Asn | Arg | Thr | Gln 90 | Thr | Asn | Leu | Thr | Glu 95 | Gly |
| Pro | Pro | Asp | Lys 100 | | | | | | | | | | | | |